(12) United States Patent
Chuang et al.

(10) Patent No.: US 12,357,226 B2
(45) Date of Patent: Jul. 15, 2025

(54) DETERMINING MEDICAL STAFFING FOR ORAL IMMUNOTHERAPY

(71) Applicant: Société des Produits Nestlé S.A., Vevey (CH)

(72) Inventors: Hans Chuang, Brisbane, CA (US); Brian Greenblatt, Brisbane, CA (US); Richard Smith, Brisbane, CA (US); Marisa Crowell, Brisbane, CA (US); Varsha Damle, Brisbane, CA (US); Chantale Bielak, Toronto (CA); Robert Grossi, Toronto (CA); Joy Mabon, Toronto (CA)

(73) Assignee: Société des Produits Nestlé S.A., Vevey (CH)

( * ) Notice: Subject to any disclaimer, the term of this patent is extended or adjusted under 35 U.S.C. 154(b) by 463 days.

(21) Appl. No.: 17/364,518

(22) Filed: Jun. 30, 2021

(65) Prior Publication Data
US 2022/0000416 A1 Jan. 6, 2022

Related U.S. Application Data

(60) Provisional application No. 63/047,216, filed on Jul. 1, 2020.

(51) Int. Cl.
*A61B 5/00* (2006.01)
*G16H 20/10* (2018.01)
*G16H 40/20* (2018.01)

(52) U.S. Cl.
CPC ............ *A61B 5/411* (2013.01); *A61B 5/4848* (2013.01); *A61B 5/742* (2013.01); *G16H 20/10* (2018.01); *G16H 40/20* (2018.01)

(58) Field of Classification Search
CPC ....... A61B 5/411; A61B 5/4848; A61B 5/742; G16H 20/10; G16H 40/20; G06Q 10/06313
(Continued)

(56) References Cited

U.S. PATENT DOCUMENTS 7,457,765 B2 * 11/2008 Thompson ..... G06Q 10/063112
705/7.14
8,435,517 B2  5/2013 Desjarlais
(Continued)

FOREIGN PATENT DOCUMENTS

WO  2010033736 A1  3/2010
WO  2014159607 A1  10/2014
(Continued)

OTHER PUBLICATIONS

Blümchen, K. et al. (2020). "P1.4: Educational Needs of Allergists in Germany: Results From a Questionnaire Focused on Physicians Managing Patients With Peanut Allergy," Deutscher Allergiekongress, 3 pages.
(Continued)

*Primary Examiner* — Joseph M Dietrich
*Assistant Examiner* — Michael T. Holtzclaw
(74) *Attorney, Agent, or Firm* — Morgan, Lewis & Bockius LLP

(57) ABSTRACT

Described herein are systems and methods for determining medical staffing requirements for administering OIT to patients. Specifically, the methods and systems disclosed herein can determine the time required by a medical staff at a given treatment location to devote to administering OIT to patients as well as the number of patients undergoing OIT over a selected time period. The methods and systems disclosed herein can further provide the time required by providers and clinical staff at a given treatment location to devote to administering OIT to patients.

10 Claims, 20 Drawing Sheets

(58) Field of Classification Search
USPC .......................................................... 600/300
See application file for complete search history.

(56) References Cited

U.S. PATENT DOCUMENTS

| | | | |
|---|---|---|---|
| 9,062,117 B2 | 6/2015 | Desjarlais | |
| 9,198,869 B2 | 12/2015 | Walser | |
| 9,221,916 B2 | 12/2015 | Desjarlais | |
| 9,266,966 B2 | 2/2016 | Desjarlais | |
| 9,492,535 B2 | 11/2016 | Walser | |
| 9,540,451 B2 | 1/2017 | Desjarlais | |
| 9,617,348 B2 | 4/2017 | Desjarlais | |
| 10,042,981 B2* | 8/2018 | Janssen | G16H 20/40 |
| 10,086,068 B2 | 10/2018 | Walser | |
| 10,134,488 B1* | 11/2018 | Bullington | G16H 40/20 |
| 10,449,118 B2 | 10/2019 | Walser | |
| D866,320 S | 11/2019 | Bennett et al. | |
| D866,321 S | 11/2019 | Bennett et al. | |
| D866,322 S | 11/2019 | Bennett et al. | |
| 10,512,686 B2 | 12/2019 | Walser | |
| 10,653,773 B2 | 5/2020 | Walser | |
| 10,918,676 B2 | 2/2021 | Raff | |
| 11,141,352 B2 | 10/2021 | Walser et al. | |
| 11,197,896 B2 | 12/2021 | Raff | |
| 2003/0050794 A1* | 3/2003 | Keck | G16H 40/20 |
| | | | 705/2 |
| 2007/0129983 A1* | 6/2007 | Scherpbier | G16H 40/20 |
| | | | 705/2 |
| 2007/0239484 A1* | 10/2007 | Arond | G06Q 10/0637 |
| | | | 705/2 |
| 2009/0089080 A1 | 4/2009 | Meisel | |
| 2010/0080814 A1 | 4/2010 | Desjarlais | |
| 2011/0054946 A1* | 3/2011 | Coulter | G16H 30/20 |
| | | | 705/2 |
| 2013/0177553 A1 | 7/2013 | Desjarlais | |
| 2013/0203966 A1 | 8/2013 | Desjarlais et al. | |
| 2013/0203967 A1 | 8/2013 | Desjarlais | |
| 2014/0212435 A1 | 7/2014 | Moore | |
| 2014/0271721 A1 | 9/2014 | Walser | |
| 2014/0271836 A1 | 9/2014 | Walser | |
| 2015/0093379 A1 | 4/2015 | Desjarlais | |
| 2015/0139985 A1 | 5/2015 | Desjarlais | |
| 2015/0343075 A1 | 12/2015 | Raff | |
| 2016/0030289 A1 | 2/2016 | Walser | |
| 2016/0051593 A1 | 2/2016 | Raff | |
| 2016/0051639 A1 | 2/2016 | Raff | |
| 2017/0021012 A1 | 1/2017 | Walser | |
| 2017/0124526 A1* | 5/2017 | Sanderford | G06Q 10/1095 |
| 2017/0335013 A1 | 11/2017 | Desjarlais | |
| 2018/0042816 A1 | 2/2018 | Walser | |
| 2018/0200361 A1 | 7/2018 | Simon | |
| 2018/0314802 A1 | 11/2018 | Dreyer | |
| 2019/0167785 A1 | 6/2019 | Dilly | |
| 2019/0175723 A1 | 6/2019 | Walser | |
| 2019/0192652 A1 | 6/2019 | Walser | |
| 2019/0247444 A1 | 8/2019 | Raff | |
| 2020/0030187 A1 | 1/2020 | Bennett | |
| 2020/0054738 A1 | 2/2020 | Adelman | |
| 2020/0129378 A1 | 4/2020 | Walser | |
| 2020/0230206 A1 | 7/2020 | Matthews | |
| 2020/0332024 A1 | 10/2020 | Desjarlais et al. | |
| 2020/0368304 A1 | 11/2020 | Birchwood | |
| 2021/0052722 A1 | 2/2021 | Walser et al. | |
| 2021/0151155 A1 | 5/2021 | Dana et al. | |
| 2021/0295985 A1* | 9/2021 | Prokle | G16H 40/20 |

FOREIGN PATENT DOCUMENTS

| | | |
|---|---|---|
| WO | 2014159609 A1 | 10/2014 |
| WO | 2015187736 A1 | 12/2015 |
| WO | 2016033094 A1 | 3/2016 |
| WO | 2018132733 A1 | 7/2018 |
| WO | 2019089978 A1 | 5/2019 |
| WO | 2020023925 A1 | 1/2020 |
| WO | 2020037151 A1 | 2/2020 |
| WO | 2020131917 A1 | 6/2020 |
| WO | 2020132341 A1 | 6/2020 |
| WO | 2020198024 A1 | 10/2020 |
| WO | 2020231843 A1 | 11/2020 |
| WO | 2020237181 A1 | 11/2020 |
| WO | 2021102186 A1 | 5/2021 |

OTHER PUBLICATIONS

Hartman, J.M. et al. (Nov. 7-11, 2019). "P-305-Reported Practice Logistics for Implementation of Subcutaneous Immunotherapy Among US-Based Allergists/Immunologists," American College of Allergy Asthma, and Immunology Annual Scientific Meeting, 1 page.

Jacobs, J.S. et al. (Feb. 2-6, 2020). "25-Reported Practice Logistics for Implementation of Subcutaneous Immunotherapy Versus Food Oral Immunotherapy Among US-Based Allergists/Immunologists," The Western Society of Allergy, Asthma and Immunology 2020 Annual Scientific Session, 1 page.

U.S. Appl. No. 17/414,288, Reyna et al., filed Jun. 15, 2021.

International Search Report and Written Opinion, mailed Nov. 3, 2021, for PCT Application No. PCT/IB2021/055885, filed Jun. 30, 2021, 10 pages.

Akram et al., "Paediatric nurses' knowledge and practice of mixing medication into foodstuff," (2012) International Journal of Pharmacy Practice, vol. 20, pp. 191-198.

Mori et al., "Oral Immunotherapy for Food-Allergic Children: A Pro-Con Debate," (2021) Frontiers in Immunology, vol. 12, Article 636612, pp. 1-15.

\* cited by examiner

OIT CAPACITY MODEL - BASE

Model Inputs

| | | CQ-2 | CQ-1 | Q1 | Q2 | Q3 | Q4 |
|---|---|---|---|---|---|---|---|
| Patient Volume | New patients starting AR101 every week | 1 | 2 | 3 | 4 | 5 | 6 |
| | Attrition: % of patients who complete updosing | 100% | | | | | |

| | | Estimated | ALG | NP/PA | RN/MA |
|---|---|---|---|---|---|
| New Pt. Prep | Pre-Work for new patients (initial consultation, benefits investigation, other preparation) | 5.0 | 0.3 | 0.3 | 4.5 |
| Initial Dose Escalation | IDE hours per patient requiring dedicated medical supervision in dedicated room or area | 5.0 | 1.3 | 1.6 | 2.2 |
| | % of patients monitored as group | 0% | | | |
| Dose Escalation | DE hours per patient per visit requiring direct medical supervision in dedicated room or area | 1.0 | 0.3 | 0.5 | 0.2 |
| | % of patients monitored as group | 0% | | | |

| | | Estimated |
|---|---|---|
| Exam Rooms | Exam rooms dedicated to peanut allergy | 1 |
| | Available hours per room per week | 40 |
| | Total hours/week | 40 |
| Capacity & Scheduling | Patient Visits (Dose Escalation plus initial therapeutic dose) | 12 |
| | Time between visits (Days) | 14 |

FIG. 2

| 20 | | Wk 1 | Wk 2 | Wk 3 |
|---|---|---|---|---|
| 21 | Total Weekly Actual Appointments | 6.0 | 6.0 | 7.0 |
| 22 | Cumulative New Patients | 1 | 2 | 3 |
| 23 | Total Patients Treated - DE | 1.0 | 1.0 | 2.0 |
| 24 | Total Cumulative Patients | 1.0 | 2.0 | 3.0 |
| 25 | Hr/Week: Prep Work | 5.0 | 5.0 | 5.0 |
| 26 | Total IDE per Week (Supervised Hours) | 5.000 | 5.000 | 5.000 |
| 27 | Total DE per Week (Supervised Hours) | 1.0 | 1.0 | 2.0 |
| 28 | Hr/Wk: Active Pt Treatment | 6.0 | 6.0 | 7.0 |
| 29 | Hr/Wk: Prep Work + Active Pt Treatment | 11.0 | 11.0 | 12.0 |

Appointment Time Calculation (rows 21–29)

FIG. 4A

| 160 | Active Patient Roster Calc | Pt Visit | | |
|---|---|---|---|---|
| 161 | Calendar Week | 1 | 2 | 3 |
| 162 | 1 | 1.0 | 1.0 | 1.0 |
| 163 | 2 | 1.0 | 1.0 | 1.0 |
| 164 | 3 | 1.0 | 1.0 | 1.0 |
| 165 | 4 | 1.0 | 1.0 | 1.0 |

FIG. 4B

| 268 | # of DE Calculation | Pt Visit | | |
|---|---|---|---|---|
| 269 | Calendar Week | 1 | 2 | 3 |
| 270 | 1 | 1.0 | 0.0 | 1.0 |
| 271 | 2 | 1.0 | 0.0 | 1.0 |
| 272 | 3 | 1.0 | 0.0 | 1.0 |
| 273 | 4 | 1.0 | 0.0 | 1.0 |

FIG. 4C

| 268 | # of DE Calculation | Pt Visit | | |
|---|---|---|---|---|
| 269 | Calendar Week | 1 | 2 | 3 |
| 270 | 1 | 1.0 | 0.0 | 1.0 |
| 271 | 2 | 1.0 | 0.0 | 1.0 |
| 272 | 3 | 1.0 | 0.0 | 1.0 |
| 273 | 4 | 1.0 | 0.0 | 1.0 |

FIG. 4D

| 9 | | 1 | 2 | 3 |
|---|---|---|---|---|
| ⇨ 10 | Number of patient starts per week | 1 | 1 | 1 |
| 11 | | | | |
| ⇨ 12 | Prep Work before patient initiation | 5 hrs | | |
| 13 | IDE (from feedback) | 5 hrs | | |
| 14 | DE (from feedback) | 1.00 hrs | | |
| 15 | | | | |
| 16 | | ALG | NP/PA | RN/Med Asst |
| 17 | IDE | 25% | 32% | 43% |
| 18 | DE | 30% | 50% | 20% |
| 19 | PREP | 5% | 5% | 90% |
| 20 | | | | |
| 21 | Total Weekly Actual Appointments | 6.0 | 6.0 | 7.0 |
| 22 | Cumulative New Patients | 1 | 2 | 3 |
| 23 | Total Patients Treated - DE | 1.0 | 1.0 | 2.0 |
| 24 | Total Cumulative Patients | 1.0 | 2.0 | 3.0 |
| ⇨ 25 | Hr/Week: Prep Work | 5.0 | 5.0 | 5.0 |
| 26 | Total IDE per Week (Supervised Hours) | 5.000 | 5.000 | 5.000 |
| 27 | Total DE per Week (Supervised Hours) | 1.0 | 1.0 | 2.0 |
| 28 | Hr/Wk: Active Pt Treatment | 6.0 | 6.0 | 7.0 |
| 29 | Hr/Wk: Prep Work + Active Pt Treatment | 11.0 | 11.0 | 12.0 |
| 30 | | | | |

FIG. 5A

| 21 | Total Weekly Actual Appointments | 6.0 | 6.0 | 7.0 |
|---|---|---|---|---|
| 22 | Cumulative New Patients | 1 | 2 | 3 |
| 23 | Total Patients Treated - DE | 1.0 | 1.0 | 2.0 |
| 24 | Total Cumulative Patients | 1.0 | 2.0 | 3.0 |
| 25 | Hr/Week: Prep Work | 5.0 | 5.0 | 5.0 |
| 26 | Total IDE per Week (Supervised Hours) | 5.000 | 5.000 | 5.000 |
| 27 | Total DE per Week (Supervised Hours) | 1.0 | 1.0 | 2.0 |
| 28 | Hr/Wk: Active Pt Treatment | 6.0 | 6.0 | 7.0 |
| 29 | Hr/Wk: Prep Work + Active Pt Treatment | 11.0 | 11.0 | 12.0 |
| 30 | | | | |
| 31 | ALL - IDE Hours / Week | 1.3 | 1.3 | 1.3 |
| 32 | ALL - DE Hours / Week | 0.3 | 0.3 | 0.6 |
| 33 | ALL - Prep Hours / Week | 0.3 | 0.3 | 0.3 |
| 34 | NP/PA - IDE Hours / Week | 1.6 | 1.6 | 1.6 |
| 35 | NP/PA - DE Hours / Week | 0.5 | 0.5 | 1.0 |
| 36 | NP/PA - Prep Hours / Week | 0.3 | 0.3 | 0.3 |
| 37 | RN/MA - IDE Hours / Week | 2.2 | 2.2 | 2.2 |
| 38 | RN/MA - DE Hours / Week | 0.2 | 0.2 | 0.4 |
| 39 | RN/MA - Prep Hours / Week | 4.5 | 4.5 | 4.5 |
| 40 | Allergist - Total Hours / Week | 1.8 | 1.8 | 2.1 |
| 41 | NP/PA - Total Hours / Week | 2.4 | 2.4 | 2.9 |
| 42 | RN/Med Asst - Total Hours / Week | 6.9 | 6.9 | 7.1 |

FIG. 5B

Patient Volume ^

NEW PATIENTS STARTING EVERY WEEK

Q3 - 19 *    Q4 - 19 *    Q1 - 20 *
                          Current Qtr

Q2 - 20 *    Q3 - 20 *    Q4 - 20 *

ATTRITION: % OF PATIENTS WHO COMPLETE UP-DOSING
*
83.3 %

FIG. 8A

New Patient Prep ^

PRE-WORK FOR NEW PATIENTS (INITIAL CONSULTATION, BENEFITS INVESTIGATION, OTHER PREPARATION)

ALG *    NP/...    RN/...    Total
                             0

FIG. 8B

Initial Dose Escalation ⌃

IDE HOURS PER PATIENT REQUIRING DEDICATED MEDICAL SUPERVISION IN DEDICATED ROOM OR AREA

| ALG * | NP/PA * | RN/MA * | Total |
|---|---|---|---|
| 3 | 0 | 0 | 3 |

% OF PATIENTS MONITORED AS GROUP

Up-Dosing ⌃

UP-DOSING HOURS PER PATIENT PER VISIT REQUIRING DIRECT MEDICAL SUPERVISION IN DEDICATED ROOM OR AREA

| ALG * | NP/PA * | RN/MA * | Total |
|---|---|---|---|
| 1 | 0 | 0 | 1 |

% OF PATIENTS MONITORED AS GROUP

```
Capacity & Scheduling                    ∧

PATIENT VISITS AFTER IDE (UP-DOSING +
FIRST MAINTENANCE DOSE)
Estimated *
12

TIME BETWEEN VISITS (DAYS)
*
14
```

FIG. 8E

```
Exam Rooms                               ∧

DEDICATED EXAM ROOMS
Estimated *
1

AVAILABLE HOURS PER ROOM PER WEEK
*
40
```

FIG. 8F

| 3 | Calendar Week | 77 | 78 | 79 |
|---|---|---|---|---|
| 4 | Number of exam rooms | 1 | 1 | 1 |
| 5 | Avail. Hr/Room | 40 | 40 | 40 |
| 6 | Hrs / Wk - Exam Rooms | 40 | 40 | 40 |
| 7 | Required Dedicated Exam Rooms: Hrs / Wk | 96.0 | 97.0 | 97.0 |
| 8 | Under/Overcapacity | Over | Over | Over |
| 9 | | 77 | 78 | 79 |
| 10 | Number of patient starts per week | 6 | 6 | 6 |
| 11 | | | | |
| 12 | Prep Work before patient initiation | | | |
| 13 | IDE (from feedback) | | | |
| 14 | DE (from feedback) | | | |
| 15 | | | | |
| 16 | | | | |
| 17 | IDE | | | |
| 18 | DE | | | |
| 19 | PREP | | | |
| 20 | | | | |
| 21 | Total Weekly Actual Appointments | 96.0 | 97.0 | 97.0 |
| 22 | Cumulative New Patients | 267 | 273 | 279 |
| 23 | Total Patients Treated - DE | 66.0 | 67.0 | 67.0 |
| 24 | Total Cumulative Patients | 267.0 | 273.0 | 279.0 |
| 25 | Hr/Week: Prep Work | 30.0 | 30.0 | 30.0 |
| 26 | Total IDE per Week (Supervised Hours) | 30.000 | 30.000 | 30.000 |
| 27 | Total DE per Week (Supervised Hours) | 66.000 | 67.000 | 67.000 |
| 28 | Hr/Wk: Active Pt Treatment | 96.0 | 97.0 | 97.0 |
| 29 | Hr/Wk: Prep Work + Active Pt Treatment | 126.0 | 127.0 | 127.0 |
| 30 | | | | |

FIG. 11

| ◢ | A | BZ | CA |
|---|---|---:|---:|
| 1 | | | |
| 2 | | | |
| 3 | Calendar Week | 77 | 78 |
| 22 | Cumulative New Patients | 267 | 273 |
| 23 | Total Patients Treated - DE | 66.0 | 67.0 |
| 24 | Total Cumulative Patients | 267.0 | 273.0 |
| 25 | Hr/Week: Prep Work | 30.0 | 30.0 |
| 26 | Total IDE per Week (Supervised Hours) | 30.000 | 30.000 |
| 27 | Total DE per Week (Supervised Hours) | 66.000 | 67.000 |
| 28 | Hr/Wk: Active Pt Treatment | 96.0 | 97.0 |
| 29 | Hr/Wk: Prep Work + Active Pt Treatment | 126.0 | 127.0 |
| 30 | | | |
| 31 | ALL - IDE Hours / Week | 7.5 | 7.5 |
| 32 | ALL - DE Hours / Week | 19.8 | 20.1 |
| 33 | ALL - Prep Hours / Week | 1.5 | 1.5 |
| 34 | NP/PA - IDE Hours / Week | 9.6 | 9.6 |
| 35 | NP/PA - DE Hours / Week | 33.0 | 33.5 |
| 36 | NP/PA - Prep Hours / Week | 1.5 | 1.5 |
| 37 | RN/MA - IDE Hours / Week | 12.9 | 12.9 |
| 38 | RN/MA - DE Hours / Week | 13.2 | 13.4 |
| 39 | RN/MA - Prep Hours / Week | 27.0 | 27.0 |
| 40 | Allergist - Total Hours / Week | 28.8 | 29.1 |
| 41 | NP/PA - Total Hours / Week | 44.1 | 44.6 |
| 42 | RN/Med Asst - Total Hours / Week | 53.1 | 53.3 |

FIG. 12

| ◢ | A | BZ | CA |
|---|---|---|---|
| 1 | ✚ | | |
| 2 | | | |
| 3 | Calendar Week | 77 | 78 |
| 4 | Number of exam rooms | 1 | 1 |
| 5 | Avail. Hr/Room | 40 | 40 |
| 6 | Hrs / Wk - Exam Rooms | 40 | 40 |
| 7 | Required Dedicated Exam Rooms: Hrs / Wk | 96.0 | 97.0 |
| 8 | Under/Overcapacity | Over | Over |
| 9 | | 77 | 78 |
| 10 | Number of patient starts per week | 6 | 6 |
| 11 | | | |
| 12 | Prep Work before patient initiation | | |
| 13 | IDE (from feedback) | | |
| 14 | DE (from feedback) | | |
| 15 | | | |
| 16 | | | |
| 17 | IDE | | |
| 18 | DE | | |
| 19 | PREP | | |
| 20 | | | |
| 21 | Total Weekly Actual Appointments | 96.0 | 97.0 |
| 22 | Cumulative New Patients | 267 | 273 |
| 23 | Total Patients Treated - DE | 66.0 | 67.0 |
| 24 | Total Cumulative Patients | 267.0 | 273.0 |
| 25 | Hr/Week: Prep Work | 30.0 | 30.0 |
| 26 | Total IDE per Week (Supervised Hours) | 30.000 | 30.000 |
| 27 | Total DE per Week (Supervised Hours) | 66.000 | 67.000 |
| 28 | Hr/Wk: Active Pt Treatment | 96.0 | 97.0 |
| 29 | Hr/Wk: Prep Work + Active Pt Treatment | 126.0 | 127.0 |
| 30 | | | |
| 31 | ALL - IDE Hours / Week | 7.5 | 7.5 |

FIG. 13

| 1 2 ◢ | A | B | C | D | E | F | G | H | I | J | K | L | M | N | O |
|---|---|---|---|---|---|---|---|---|---|---|---|---|---|---|---|
| 1 | | | | | | | | | | | | | | | |
| 2 | | | | | | | | | | | | | | | |
| 3 | Calendar Week | 1 | 2 | 3 | 4 | 5 | 6 | 7 | 8 | 9 | 10 | 11 | 12 | 13 | 14 |
| 330 | 61 | 5.0 | 0.0 | 5.0 | 0.0 | 5.0 | 0.0 | 5.0 | 0.0 | 5.0 | 0.0 | 5.0 | 0.0 | 5.0 | 0.0 |
| 331 | 62 | 5.0 | 0.0 | 5.0 | 0.0 | 5.0 | 0.0 | 5.0 | 0.0 | 5.0 | 0.0 | 5.0 | 0.0 | 5.0 | 0.0 |
| 332 | 63 | 5.0 | 0.0 | 5.0 | 0.0 | 5.0 | 0.0 | 5.0 | 0.0 | 5.0 | 0.0 | 5.0 | 0.0 | 5.0 | 0.0 |
| 333 | 64 | 5.0 | 0.0 | 5.0 | 0.0 | 5.0 | 0.0 | 5.0 | 0.0 | 5.0 | 0.0 | 5.0 | 0.0 | 5.0 | 0.0 |
| 334 | 65 | 5.0 | 0.0 | 5.0 | 0.0 | 5.0 | 0.0 | 5.0 | 0.0 | 5.0 | 0.0 | 5.0 | 0.0 | 5.0 | 0.0 |
| 335 | 66 | 6.0 | 0.0 | 6.0 | 0.0 | 6.0 | 0.0 | 6.0 | 0.0 | 6.0 | 0.0 | 6.0 | 0.0 | 6.0 | 0.0 |
| 336 | 67 | 6.0 | 0.0 | 6.0 | 0.0 | 6.0 | 0.0 | 6.0 | 0.0 | 6.0 | 0.0 | 6.0 | 0.0 | 6.0 | 0.0 |
| 337 | 68 | 6.0 | 0.0 | 6.0 | 0.0 | 6.0 | 0.0 | 6.0 | 0.0 | 6.0 | 0.0 | 6.0 | 0.0 | 6.0 | 0.0 |
| 338 | 69 | 6.0 | 0.0 | 6.0 | 0.0 | 6.0 | 0.0 | 6.0 | 0.0 | 6.0 | 0.0 | 6.0 | 0.0 | 6.0 | 0.0 |
| 339 | 70 | 6.0 | 0.0 | 6.0 | 0.0 | 6.0 | 0.0 | 6.0 | 0.0 | 6.0 | 0.0 | 6.0 | 0.0 | 6.0 | 0.0 |
| 340 | 71 | 6.0 | 0.0 | 6.0 | 0.0 | 6.0 | 0.0 | 6.0 | 0.0 | 6.0 | 0.0 | 6.0 | 0.0 | 6.0 | 0.0 |
| 341 | 72 | 6.0 | 0.0 | 6.0 | 0.0 | 6.0 | 0.0 | 6.0 | 0.0 | 6.0 | 0.0 | 6.0 | 0.0 | 6.0 | 0.0 |
| 342 | 73 | 6.0 | 0.0 | 6.0 | 0.0 | 6.0 | 0.0 | 6.0 | 0.0 | 6.0 | 0.0 | 6.0 | 0.0 | 6.0 | 0.0 |
| 343 | 74 | 6.0 | 0.0 | 6.0 | 0.0 | 6.0 | 0.0 | 6.0 | 0.0 | 6.0 | 0.0 | 6.0 | 0.0 | 6.0 | 0.0 |
| 344 | 75 | 6.0 | 0.0 | 6.0 | 0.0 | 6.0 | 0.0 | 6.0 | 0.0 | 6.0 | 0.0 | 6.0 | 0.0 | 6.0 | 0.0 |
| 345 | 76 | 6.0 | 0.0 | 6.0 | 0.0 | 6.0 | 0.0 | 6.0 | 0.0 | 6.0 | 0.0 | 6.0 | 0.0 | 6.0 | 0.0 |
| 346 | 77 | 6.0 | 0.0 | 6.0 | 0.0 | 6.0 | 0.0 | 6.0 | 0.0 | 6.0 | 0.0 | 6.0 | 0.0 | 6.0 | 0.0 |
| 347 | 78 | 6.0 | 0.0 | 6.0 | 0.0 | 6.0 | 0.0 | 6.0 | 0.0 | 6.0 | 0.0 | 6.0 | 0.0 | 6.0 | 0.0 |
| 348 | 79 | 6.0 | 0.0 | 6.0 | 0.0 | 6.0 | 0.0 | 6.0 | 0.0 | 6.0 | 0.0 | 6.0 | 0.0 | 6.0 | 0.0 |

FIG. 14

DETERMINING MEDICAL STAFFING FOR ORAL IMMUNOTHERAPY

CROSS-REFERENCE TO RELATED APPLICATIONS

This application claims the priority benefit of U.S. Provisional Application No. 63/047,216, filed Jul. 1, 2020, the entire disclosure of which is hereby incorporated by reference.

FIELD OF THE INVENTION

This relates generally to medical staffing for oral immunotherapy ("OIT"), and more specifically to systems and methods for determining medical staff capacity and scheduling for administering oral immunotherapy to patients.

BACKGROUND OF THE INVENTION

Oral immunotherapy ("OIT") is a medical treatment where an allergic individual to certain foods is fed an increasing amount of the same allergen that causes the allergic reactions in order to desensitize the individual to the allergen. The goal of oral immunotherapy is to increase the threshold that triggers an allergic reaction such that the individual has protection against accidental ingestion of the allergen. During oral immunotherapy, the immune system is retrained to tolerate allergens through consuming small amounts of the allergen that increases over time.

Because OIT can involve multiple visits to a treatment location for subsequent dose escalation or up-dosing the allergic individual, the treatment location should be properly staffed to adequately administer the OIT to the patient throughout the entire course of his or her OIT sessions. Typical medical staff for OIT includes at least one provider (i.e., a doctor, nurse practitioner, or physician's assistant) and at least one clinical staff member (i.e., registered nurse or a medical assistant). The staffing requirements become more complicated as additional new patients start OIT at the treatment locations. In addition, the treatment location may not have a designated exam room or area or may only have one exam room or area for administering the OIT dosing to the patients.

SUMMARY OF THE INVENTION

As described above, properly determining and managing the medical staff for an OIT treatment location is important for the adequate, safe, and efficient administration of OIT to patients. There are a number of factors that can affect the medical staff's capacity to efficiently administer OIT to a plurality of patients including, but not limited, to (1) how many new patients are starting OIT each week at a given treatment location; (2) how much time is required by the medical staff to prepare each new patient to start OIT; (3) how many rooms or areas are available at the treatment location designated to OIT and how many available hours do these rooms/areas have per week; (4) how much time is required by medical staff to administer an initial dose escalation ("IDE") of OIT for each new patient (what percentage of these patients can be monitored as a group); (5) how much time is required by medical staff to administer each subsequent dose (i.e., dose escalation or up-dosing) ("DE") for each patient (what percentage of these patients can be monitored as a group; (6) the number of visits to the treatment location required for each patient to complete OIT; (7) how much time is there between visits to the treatment location for OIT; and (8) the percentage of patients who complete OIT.

Applicants have discovered systems and methods for determining medical staffing requirements for administering OIT to patients that take into account at least all of the factors listed in the previous paragraph. Specifically, the methods and systems disclosed herein can determine the time required by a medical staff at a given treatment location to devote to administering OIT to patients as well as the number of patients undergoing OIT over a selected time period. The methods and systems disclosed herein can further provide the time required by providers and clinical staff at a given treatment location to devote to administering OIT to patients.

In some embodiments, a method for determining medical staffing requirements for administering medical treatment to patients at a treatment location includes: receiving a number of patients that are starting medical treatment per a predetermined time period at a treatment location; receiving a number of visits to the treatment location per patient to complete the medical treatment; receiving an amount of time between visits to the treatment location per patient; determining a number of patients undergoing medical treatment at the treatment location over a selected time period based on at least the number of patients starting medical treatment each week at the treatment location, the number of visits to the treatment location per patient to complete the medical treatment, and the amount of time between visits to the treatment location per patient; receiving an estimated amount of time required by medical staff to administer medical treatment per patient per visit to the treatment location; determining time required by medical staff to administer medical treatment to the patients at the treatment location over the selected time period based on at least the number of patients undergoing medical treatment at the treatment location for the selected time period and the estimated amount of time required by medical staff to administer medical treatment per patient per visit at the treatment location; and displaying a graphical indication of the time required by medical staff to administer medical treatment to the patients at the treatment location over the selected time period.

In some embodiments, the method further includes receiving a number of areas at the treatment location dedicated to the medical treatment and an amount of available treatment time per area per the predetermined time period; determining available treatment time for all areas at the treatment location dedicated to the medical treatment over the selected time period; and displaying a graphical indication of the available treatment time for all areas at the treatment location dedicated to the medical treatment over the selected time period. In some embodiments, the method further includes determining when the time required by medical staff to administer medical treatment to the patients exceeds the available treatment time for all areas at the treatment location dedicated to the medical treatment over the selected period of time; and displaying a graphical indication that the time required by medical staff to administer medical treatment to the patients exceeds the available treatment time for all areas at the treatment location dedicated to the medical treatment over the selected period of time. In some embodiments, the method further includes displaying a graphical indication of the number of patients undergoing medical treatment at the treatment location over the selected time period. In some embodiments, the method further includes receiving an estimated percentage of patients who complete the medical treatment, wherein determining the number of patients undergoing medical treatment at the treatment location over the selected time period is further based on the estimated percentage of patients who complete the medical treatment.

In some embodiments, receiving the estimated amount of time required by medical staff to administer medical treatment per patient per visit to the treatment location comprises at least one of: receiving an estimated amount of time required by medical staff to prepare a patient to start to start the medical treatment; receiving an estimated amount of time required by medical staff to administer an initial dose of medical treatment to a patient; receiving an estimated amount of time required by medical staff to administer subsequent dose escalation of medical treatment per patient per visit. In some embodiments, receiving an estimated amount of time required by medical staff to administer an initial dose of medical treatment to a patient and receiving an estimated amount of time required by medical staff to administer subsequent dose escalation of medical treatment to a patient comprise receiving an estimated percentage of patients being monitored as a group. In some embodiments, the method includes determining when steady state occurs, wherein steady state is when a rate of new patients equals a rate of patients completing the medical treatment. In some embodiments, the method includes notifying the medical staff of the time required by medical staff to administer medical treatment to the patients at the treatment location over the selected time period. In some embodiments, the medical staff comprises at least one of a doctor, a nurse practitioner or physician's assistant, or a registered nurse or medical assistant. In some embodiments, the medical treatment is oral immunotherapy.

In some embodiments, a system for determining medical staffing requirements for administering medical treatment to patients at a treatment location, the system configured to: receive a number of patients that are starting medical treatment per a predetermined time period at a treatment location; receive a number of visits to the treatment location per patient to complete the medical treatment; receive an amount of time between visits to the treatment location per patient; determine a number of patients undergoing medical treatment at the treatment location over a selected time period based on at least the number of patients starting medical treatment each week at the treatment location, the number of visits to the treatment location per patient to complete the medical treatment, and the amount of time between visits to the treatment location per patient; receive an estimated amount of time required by medical staff to administer medical treatment per patient per visit to the treatment location; determine time required by medical staff to administer medical treatment to the patients at the treatment location over the selected time period based on at least the number of patients undergoing medical treatment at the treatment location for the selected time period and the estimated amount of time required by medical staff to administer medical treatment per patient per visit at the treatment location; and display a graphical indication of the time required by medical staff to administer medical treatment to the patients at the treatment location over the selected time period.

In some embodiments, a non-transitory computer readable storage medium storing one or more programs, the one or more programs comprising instructions, which when executed by an electronic device, cause the device to: receive a number of patients that are starting medical treatment per a predetermined time period at a treatment location; receive a number of visits to the treatment location per patient to complete the medical treatment; receive an amount of time between visits to the treatment location per patient; determine a number of patients undergoing medical treatment at the treatment location over a selected time period based on at least the number of patients starting medical treatment each week at the treatment location, the number of visits to the treatment location per patient to complete the medical treatment, and the amount of time between visits to the treatment location per patient; receive an estimated amount of time required by medical staff to administer medical treatment per patient per visit to the treatment location; determine time required by medical staff to administer medical treatment to the patients at the treatment location over the selected time period based on at least the number of patients undergoing medical treatment at the treatment location for the selected time period and the estimated amount of time required by medical staff to administer medical treatment per patient per visit at the treatment location; and display a graphical indication of the time required by medical staff to administer medical treatment to the patients at the treatment location over the selected time period.

In some embodiments, any one or more of the characteristics of any one or more of the systems, methods, and/or computer-readable storage mediums recited above may be combined, in whole or in part, with one another and/or with any other features or characteristics described elsewhere herein.

BRIEF DESCRIPTION OF THE DRAWINGS

The invention will now be described, by way of example only, with reference to the accompanying drawings, in which:

FIG. 2 depicts an exemplary graphical user interface for receiving inputs for the medical staffing system, in accordance with some embodiments.

FIG. 4A depicts a second exemplary spreadsheet for calculating/determining various components for the medical staffing system, in accordance with some embodiments.

FIG. 4B depicts a third exemplary spreadsheet for calculating/determining various components for the medical staffing system, in accordance with some embodiments.

FIG. 4C depicts a fourth exemplary spreadsheet for calculating/determining various components for the medical staffing system, in accordance with some embodiments.

FIG. 4D depicts a fifth exemplary spreadsheet for calculating/determining various components for the medical staffing system, in accordance with some embodiments.

FIG. 5A depicts a sixth exemplary spreadsheet for calculating/determining various components for the medical staffing system, in accordance with some embodiments.

FIG. 5B depicts a seventh exemplary spreadsheet for calculating/determining various components for the medical staffing system, in accordance with some embodiments.

FIGS. 8A-F depict an exemplary graphical user interfaces for receiving inputs for the medical staffing system, in accordance with some embodiments.

FIG. 11 depicts an exemplary spreadsheet for calculating/determining the time required by medical staff to administer medical treatment to the patients at the treatment location at peak week in accordance with the Example described herein.

FIG. 12 depicts an exemplary spreadsheet for calculating/determining the time required by medical staff specialty to administer medical treatment to the patients at the treatment location at peak week in accordance with the Example described herein.

FIG. 13 depicts an exemplary spreadsheet for calculating/determining the available treatment time for all areas at the treatment location dedicated to the medical treatment at peak week in accordance with the Example described herein.

FIG. 14 depicts an exemplary spreadsheet for calculating/determining the number of patients undergoing medical treatment at the treatment location at peak week in accordance with the Example described herein.

DETAILED DESCRIPTION OF THE INVENTION

Figure 1A:
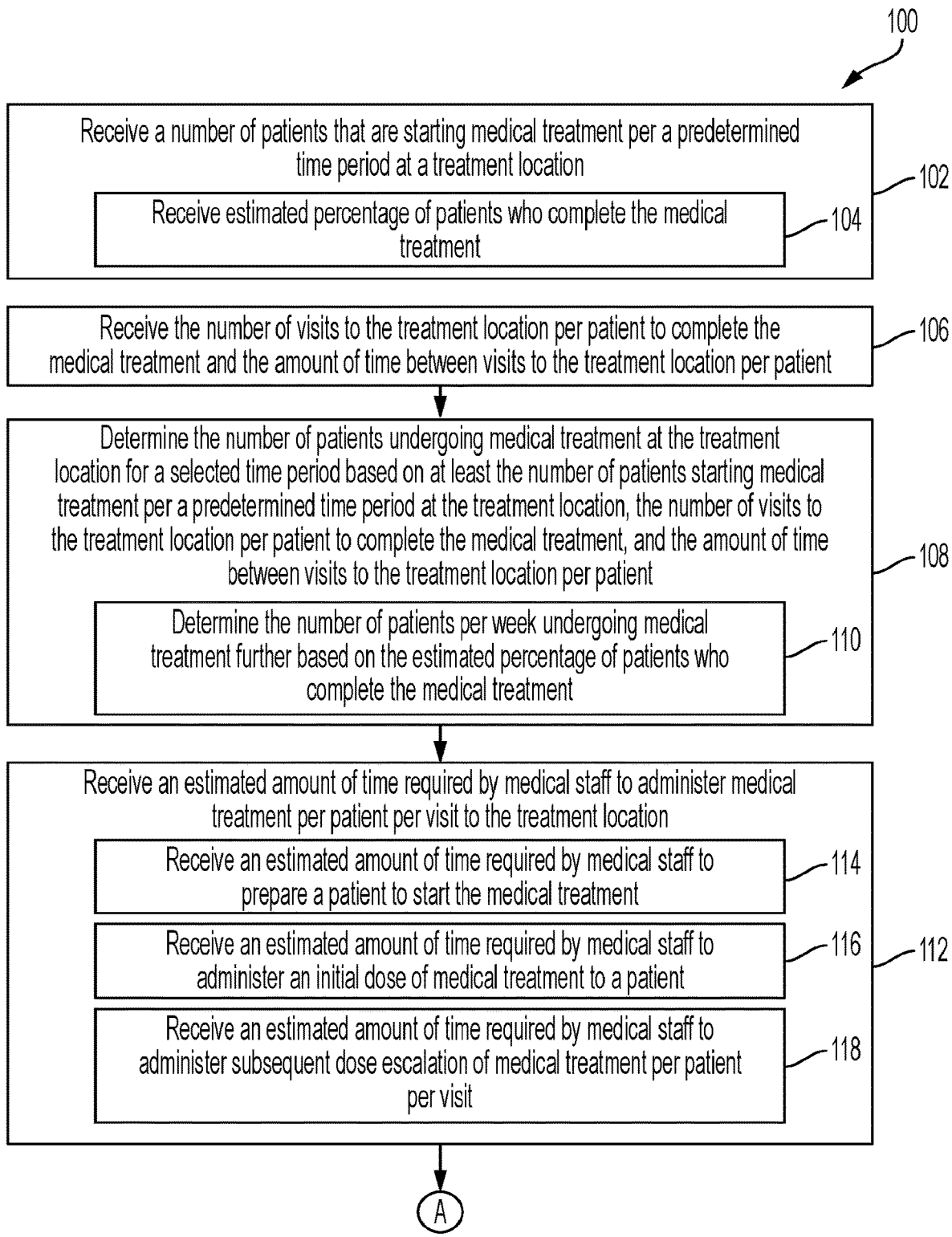
FIG. 1A depicts a flowchart representing an exemplary method for determining medical staffing requirements for administering medical treatment to patients, in accordance with some embodiments.

Described herein are exemplary embodiments of systems for determining staffing requirements for administering medical treatment to patients, which may address the problems and shortcomings described above. Such systems can help medical staff and office managers evaluate and plan for office capacity to prepare for the potential inflow of patients being treated at a treatment location including both the time required for medical staff to administer the medical treatment and designated area space (e.g., examination rooms) at a treatment location. In some embodiments, the medical treatment may be oral immunotherapy, but this application is not limited to such treatment.

The medical staffing system can ensure that medical treatment can safely be administered to patients by highlighting the internal resources that may be needed during medical treatment. For example, the system can help a treatment location consider how much medical staff time is needed to appropriately prepare patients to receive medical treatment and then to safely administer the treatment for each visit to the treatment location. In accordance with treatment location practice dynamics, the medical staff time can be divided between doctors (e.g., allergists), nurse practitioner/physician assistants, and registered nurses/medical assistants. Separately, this system can help assess the areas or spaces in the treatment location that will be needed to safely administer the medical treatment for treatment locations to evaluate potential space/area constraint considerations in the future based on estimated patient volume.

The medical staffing system may be any device or system comprising one or more computer processors configured to receive data and/or inputs, assess and/or process the received data/input, and to generate and transmit one or more output signals in accordance with the results of the medical staffing system. In some embodiments, medical staffing system may be provided, in whole or in part, as all or part of a desktop computing device, laptop, tablet, mobile electronic device, dedicated medical staffing processing device, computing module, processor, server, cloud computing system, distributed computing system, or the like. In some embodiments, medical staffing system may be provided locally with respect to a treatment location, while in some embodiments, the medical staffing system may be provided remotely from a treatment location (e.g., outside the treatment location, elsewhere in a hospital, at a remote server location, etc.). In some embodiments, the medical staffing system can be utilized by a field based Practice Account Manager ("PAM") working on a wireless device with the HCP or office manager in providing inputs into the medical staffing system.

In some embodiments, the staffing system may be configured to receive input data from a user of the system and to process the input data to determine medical staffing requirements for administering medical treatment based on the input data received. In some embodiments, staffing system may be configured to determine staffing requirements for administering a given medical treatment in accordance with the techniques discussed below with reference to FIGS. 1A-1B.

FIG. 1 depicts a flowchart representing an exemplary method 100 for determining medical staffing requirements for administering medical treatment to patients at a treatment location, in accordance with some embodiments. As described below in detail, method 100 may enable a medical staffing system to receive a number of patients that are starting medical treatment per a predetermined time period at a treatment location; receive a number of visits to the treatment location per patient to complete the medical treatment; receive an amount of time between visits to the treatment location per patient; determine a number of patients undergoing medical treatment at the treatment location over a selected time period based on at least the number of patients starting medical treatment each week at the treatment location, the number of visits to the treatment location per patient to complete the medical treatment, and the amount of time between visits to the treatment location per patient; receive an estimated amount of time required by medical staff to administer medical treatment per patient per visit to the treatment location; determine time required by medical staff to administer medical treatment to the patients at the treatment location over the selected time period based on at least the number of patients undergoing medical treatment at the treatment location for the selected time period and the estimated amount of time required by medical staff to administer medical treatment per patient per visit at the treatment location; and display a graphical indication of the time required by medical staff to administer medical treatment to the patients at the treatment location over the selected time period. In some embodiments, the medical staff can include at least one doctor (e.g., allergist), at least one nurse practitioner or physician's assistant, and/or at least one registered nurse or medical assistant.

In some embodiments, method 100 may be carried out, in whole or in part, by one or more of the components of the medical staffing system. In some embodiments, any one or more of the aspects of method 100 may be combined, in whole or in part, with any one or more of the systems, methods, devices, and/or techniques described elsewhere herein. The system may receive a variety inputs. These inputs can be from user input, another computer, and/or extracted from a data source (e.g., a document) sent to the staffing system.

At block 102, in some embodiments, the system may receive a number of patients that are starting medical treatment per a predetermined time period at a treatment location. In some embodiments, the system can receive the number of patients that are starting OIT per the predetermined time period at the treatment location The predetermined time period can be a day, a week, a month, a year, among others, and can also be each day, each week, or each month within a given quarter. In some embodiments, the system may only allow for the same number of patients weekly in a particular quarter (i.e., in the Inputs Patient Volume section, 1 patient in CQ-2 quarter means one new patient every week for that quarter). For example, the number of patients that are starting medical treatment per a predetermined time period at the treatment location (i.e., patient volume) can include the number of new patients that are starting the medical treatment each week within a particular quarter as shown in FIG. 2. FIG. 2 is an exemplary graphical user interface for receiving inputs into the medical staffing system. For example, a user can enter an estimated number of patients that are starting the medical treatment each week for a given quarter in the provided space in the user interface. As shown in FIG. 2, this can include an estimate for the number of new patients per week that are expected for the two previous quarters (CQ-2, CQ-1), and the current and future quarters (Q1-Q4). In addition, FIG. 8A is an exemplary graphical user interface for receiving new patients starting medical treatment every week as well as the attrition percentage. In some embodiments, the outputs or displays of the system can provide graphical indications of the current and future quarters, but these outputs/displays can account for prior quarter new starts in the system's calculations.

In some embodiments, receiving a number of patients that are starting medical treatment per a predetermined time period at a treatment location includes receiving an estimated percentage of patients who complete the medical treatment. The estimated percentage of patients who complete the medical treatment (i.e., attrition rate) can refer to the percentage of patients who successfully go through the entire medical treatment process. In some embodiments, this percentage can refer to the percentage of patients who successfully go through the whole up-dosing protocol for OIT (i.e., the estimated percentage of patients who complete the OIT). As shown in FIG. 2, a user can enter the attrition of patients completing the medical treatment in the provided space in the graphical user interface.

At block 106, in some embodiments, the system can receive the number of visits to the treatment location per patient to complete the medical treatment as well as an amount of time between visits to the treatment location per patient during medical treatment. The number of visits to complete the medical treatment as well as the amount of time between visits can be dependent on the type of medical treatment. In some embodiments, the number of visits to the treatment location per patient to complete the medical treatment can be the number of visits after the initial dose of medical treatment (i.e., the subsequent up dosing steps and the first maintenance dose, if any). For example, the standard number of visits for a patient being administered Palforzia for peanut allergies is 12, with 11 up-dosing steps plus the first therapeutic maintenance dose. Users of the system can have the option to enter or adjust the visits and time between visits based on the medical treatment and/patient.

The amount of time between visits for each patient can be the amount of time (e.g., days) estimated between each visit to the treatment location for a typical or standard patient. This input can be the number of days a typical patient at a given treatment location would require between visits. The purpose for receiving the number of visits for each patient as well as the time between visits can be to account for the "fluidity" of the medical treatment, where a typical patient in a healthcare personnel setting might take more steps to complete the up-dosing protocol, thereby potentially dragging the treatment process out longer between the standard every X amount of day visit due to logistics, tolerance, or other issues. For example, FIGS. 2 and 8E illustrate that a user can enter an estimated number of patient visits to complete the medical treatment and time between visits (i.e., capacity and scheduling).

At block 108, in some embodiments, the system can determine the number of patients undergoing medical treatment at the treatment location over a selected time period based on at least the number of patients starting medical treatment per a predetermined time period at the treatment location, the number of visits to the treatment location per patient to complete the medical treatment, and the amount of time between visits to the treatment location per patient. In some embodiments, determining the number of patients undergoing medical treatment at the treatment location over a selected time period can be further based on the estimated percentage of patients who complete the medical treatment as shown in block 110.

Figure 3:
FIG. 3 depicts a first exemplary spreadsheet for calculating/determining various components for the medical staffing system, in accordance with some embodiments.

The following provides an example calculation for determining the number of patients undergoing medical treatment at a treatment location over a selected period of time. As shown in FIG. 3, the estimated number of new patients per quarter per week that the system receives can be stored in the system (shown in row 10). Calendar Week 1 in FIG. 3 can be the first week of the CQ-2 quarter (two quarters ago from the current quarter), and each quarter can have 13 weeks, in which every week can have the same number of patients starting the medical treatment based on the input received by the system. FIG. 4A provides an example of various appointment times that are calculated based on the inputs the systems received in FIG. 2. FIG. 4A also shows the total cumulative patients which is the total number of patients that are currently being treated by a treatment location, regardless if they're coming into the treatment location during that particular week or not. FIG. 4B illustrates an example of one way the system can determine the number of patients undergoing medical treatment at the treatment location. Specifically, the sum of patients can be summed up diagonally to determine the current number of patients that are being treated. The number of patients undergoing medical treatment can also be subject to the attrition curve (i.e., estimated percentage of patients who complete the treatment. This attrition curve can apply to the hours of the patients, not the number of patients itself. In some embodiments, the system can also determine when steady state occurs. Steady state can refer to when the rate of new patients starting medical treatment is equivalent to the rate of patients completing the medical treatment.

At block 112, in some embodiments, the system can receive an estimated amount of time required by medical staff to administer medical treatment per patient per visit to the treatment location. In some embodiments, the estimated amount of time required by medical staff to administer medical treatment per patient per visit to the treatment location can include receiving an estimated amount of time required by medical staff to prepare a patient to start the medical treatment as shown in block 114. In some embodiments, this preparation or pre-work for new patients includes the time required before the actual medical treatment begins (e.g., up-dosing treatment of OIT begins). This preparation or pre-work for new patients can include an initial consultation with doctors (e.g., allergist), nurse practitioner or physician's assistant, and/or a registered nurse or medical assistant, a benefits investigation, and/or other preparations (e.g., insurance paperwork, scheduling, etc.). As such, receiving an estimated amount of time required by medical staff to prepare a patient to start the medical treatment can include receiving an estimated amount of time required by at least one doctor (e.g., allergist or "ALG"), at least one nurse practitioner ("NP") or physician's assistant ("PA"), and at least one registered nurse ("RN") or medical assistant ("MA") to prepare each new patient to start the medical treatment (e.g., OIT). In some embodiments, only one pre-work or preparation visit is required by the patients.

As shown in FIG. 2 and FIG. 8B, the total estimated time for the medical staff of preparation work required for new patients can be input into the graphical user interface (labeled as "New Pt. Prep."). In some embodiments, the estimated time for a doctor, a nurse practitioner or physician's assistant, or a registered nurse or medical assistant of preparation work required for new patients can be input into the user interface. In some embodiments, if three of the four (i.e., total, doctor, nurse practitioner or physician's assistant, and registered nurse or medical assistant) estimated time inputs for the medical staff are input into the system, the system can calculate the other estimated time input. For example, for the new patient prep-work, if a user inputs the estimated total amount of time for the medical staff, the estimated time for a doctor, and the estimated time for a nurse practitioner of a physician's assistant, the staffing system can calculate the estimated time for the registered nurse or medical assistant by subtracting the estimated time for a doctor and the nurse practitioner or physician's assistant from the estimated total amount of time for the medical staff (i.e., RN/MA time=Estimated total time−ALG time−NP/PA time). In some embodiments, the total estimated time for new patient prep-work can be calculated from the sum of the doctor's time, nurse practitioner or physician's assistant's time, and the registered nurse or medical assistant's time. For example, a user can input the time required for the doctor's, nurse practitioners or physician's assistant, and the registered nurse or medical assistant, and the system can calculate the total or sum of the medical staff time.

Figure 1B:
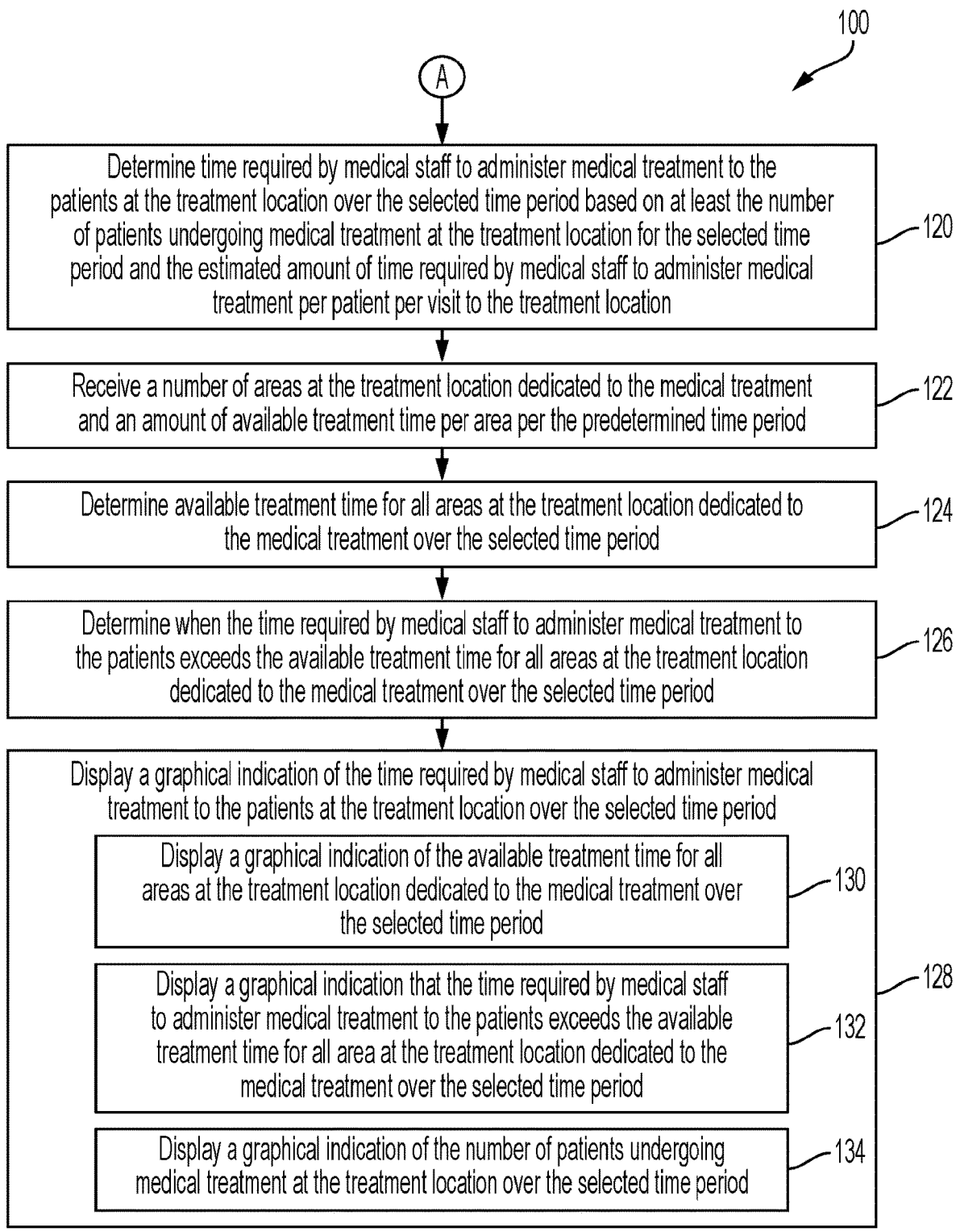
FIG. 1B is a continuation of the flowchart of FIG. 1A

In some embodiments, the estimated amount of time required by medical staff to administer medical treatment per patient per visit to the treatment location can also include receiving the estimated amount of time required by medical staff to administer an initial dose of medical treatment to a patient as shown in block 116 in FIG. 1A. In some embodiments, the estimated amount of time required by medical staff to administer an initial dose of the medical treatment can include the time required by the medical staff to administer a drug for OIT on the initial treatment day. For example, for the drug Palforzia, this can be an initial dose starting from 0.5 mg to 6 mg on the initial treatment day. In some embodiments, receiving an estimated amount of time required by medical staff to administer the initial dose of medical treatment to a patient can include receiving an estimated amount of time required by an allergist, a nurse practitioner or physician's assistant, and a registered nurse or medical assistant to administer the initial dose of medical treatment. In some embodiments, only one initial dose visit is required by the patients.

As shown in FIG. 2 and FIG. 8C, the total estimated time required for the medical staff to administer an initial dose of the medical treatment can be input into the graphical user interface (labeled as "Initial Dose Escalation"). In some embodiments, the estimated time for a doctor, a nurse practitioner or physician's assistant, or a registered nurse or medical assistant of initial dose escalation required for each patient can be input into the user interface. Similar to prep-work, if three of the four (i.e., total, doctor, nurse practitioner or physician's assistant, and registered nurse or medical assistant) estimated time inputs for the medical staff are input into the system, the system can calculate the other estimated time input. For example, for initial dose administering, if a user inputs the estimated total amount of time for the medical staff, the estimated time for a doctor, and the estimated time for a nurse practitioner of a physician's assistant, the staffing system can calculate the estimated time for the registered nurse or medical assistant by subtracting the estimated time for a doctor and the nurse practitioner or physician's assistant from the estimated total amount of time for the medical staff (i.e., RN/MA time=Estimated total time−ALG time−NP/PA time). In some embodiments, the total estimated time for initial dose administration can be calculated from the sum of the doctor's time, nurse practitioner or physician's assistant's time, and the registered nurse or medical assistant's time required. For example, a user can input the time required for the doctor's, nurse practitioners or physician's assistant, and the registered nurse or medical assistant, and the system can calculate the total or sum of the medical staff time.

In some embodiments, the system can receive an estimated percentage of patients being monitored as a group during administration of the initial dose of medical treatment in an area dedicated to the medical treatment. For example, some medical treatments allow for multiple patients to be administered treatment at the same time. As such, fewer hours, manpower, and space requirements would be needed to administer such treatment. In some embodiments, the staffing system can take this into account during the time required by medical staff to administer an initial dose of medical treatment for each patient in the area dedicated to medical treatment.

In some embodiments, the estimated amount of time required by medical staff to administer medical treatment per patient per visit to the treatment location can include receiving the estimated amount of time required to administer subsequent dose escalation of medical treatment to per patient per visit as shown in block 118. In some embodiments, the estimated amount of time required by medical staff to administer subsequent dose escalation of the medical treatment can include the time required by the medical staff to administer each of the dosing steps (and in some embodiments, the first therapeutic maintenance dose) for which administration and/or observation in a treatment location is required. In some embodiments, receiving an estimated amount of time required by medical staff to administer subsequent dose escalation can include receiving an estimated amount of time required by an allergist, a nurse practitioner or physician's assistant, and a registered nurse or medical assistant to administer a subsequent dose (i.e., up-dosing step) of medical treatment per patient per visit.

As shown in FIG. 2 and FIG. 8D, the total estimated time required for the medical staff to administer subsequent dose escalation of the medical treatment per patient per visit can be input into the user interface (labeled as "Dose Escalation" or "Updosing"). In some embodiments, the estimated time for a doctor, a nurse practitioner or physician's assistant, or a registered nurse or medical assistant of subsequent dose escalation per patient per visit can be input into the user interface. Similar to prep-work, if three of the four (i.e., total, doctor, nurse practitioner or physician's assistant, and registered nurse or medical assistant) estimated time inputs for the medical staff are input into the system, the system can calculate the other estimated time input. For example, for subsequent dose escalation, if a user inputs the estimated total amount of time for the medical staff, the estimated time for a doctor, and the estimated time for a nurse practitioner of a physician's assistant, the staffing system can calculate the estimated time for the registered nurse or medical assistant by subtracting the estimated time for a doctor and the nurse practitioner or physician's assistant from the estimated total amount of time for the medical staff (i.e., RN/MA time=Estimated total time−ALG time−NP/PA time). In some embodiments, the total estimated time for subsequent dosing can be calculated from the sum of the doctor's time, nurse practitioner or physician's assistant's time, and the registered nurse or medical assistant's time required.

In some embodiments, the system can receive an estimated percentage of patients being monitored as a group during administration of subsequent dose escalation of medical treatment. For example, some medical treatments allow for multiple patients to be administered treatment at the same time. As such, fewer hours, manpower, and space requirements would be needed to administer such treatment. In some embodiments, the staffing system can take this into account during the time required by medical staff to administer a subsequent dose of medical treatment per patient per visit. In some embodiments, the estimated percentage of patients being monitored as a group for initial dose administration and subsequent dose escalation can be the same or different.

At block 120, in some embodiments, the system can determine the time required by medical staff to administer medical treatment to the patients at the treatment location over the selected time period based on at least the number of patients undergoing medical treatment at the treatment location for the selected time period and the estimated amount of time required by medical staff to administer medical treatment per patient per visit to the treatment location.

The following provides an example calculation for determining the time required by medical staff to administer medical treatment to the patients at the treatment location over the selected time period. As shown in FIG. 3, the estimated number of new patients per quarter per week that the system receives can be stored in the system. Calendar Week 1 in FIG. 3 can be the first week of the CQ-2 quarter (two quarters ago from the current quarter), and each quarter can have 13 weeks, in which every week can have the same number of patients starting the medical treatment. The system can then calculate the appointment time per patients based on the inputs the system receives. For example, the amount of preparation time required by medical staff to prepare each patient to start the medical treatment per week, the amount of time required by medical staff to administer an initial dose of medical treatment for each patient, and the amount of time required by medical staff to administer subsequent dose escalation per patient per visit can be calculated.

From the hypothetical example shown in FIG. 4A, the total weekly actual appointments in Week 1 can be 6 hours total. Five hours of supervised initial dose of medical treatment (with one Week 1 patient) and one hour of supervised subsequent dose escalation with one patient (with one Week 1 patient). In Week 3, the hours have jumped up to 7 hours total. These 7 hours include five hours of supervised initial dose escalation (with one Week 3 patient), one hour of subsequent dose escalation (with one Week 3 patient), and one hour of subsequent dose escalation (with the returning Week 1 patient). FIG. 4A also shows the cumulative new patients which is the number of cumulative new patients the given treatment location will have per week. The total patients treated—DE in FIG. 4A refers to the total hours of subsequent dose escalation of the medical treatment by medical staff for the patients per week. An example of this calculation is shown in FIG. 4C. As shown in FIG. 4C, the calendar week can be shown across the top with patient cohorts down the rows (i.e., each row representing a new cohort that starts treatment). As an example, in Week 1, there is one patient doing subsequent dose escalation of the medical treatment so the number is one. In Week 2, since the time between visits is 14 days as shown in FIG. 2, the same patient does not have to come in to the treatment location for his dose escalation, hence the number is 0. In Week 3, the patient comes back to the treatment location for his/her next dose and therefore would be counted again as shown in FIG. 4C as 1 in Week 3. These patients can be summed up diagonally as shown in FIG. 4D. It should be noted that these hours of subsequent dose escalation can be subject to the attrition curve (i.e., percentage of patients who complete the medical treatment). Accordingly, the patients and therefore hours per week required by medical staff to administer medical treatment can be decreased or fall, in some embodiments, according to the attrition curve.

In order to calculate the amount of preparation time per week required by medical staff to prepare each new patient to start the medical treatment as shown in FIG. 4A, the system can multiply the received estimated amount of time required by medical staff to prepare each patient to start the medical treatment by the received number of patients starting medical treatment for the given week. The following provides an example of the calculation for the amount of preparation time (per week) required by medical staff to prepare each new patient to start the medical treatment. After the system receives the various inputs shown in FIG. 2, the weekly preparation hours (row 12) before a patient starts dose escalation shown in FIG. 5A can be multiplied by the number of new patients anticipated in the next week (row 10) to calculate the amount of preparation time for the current week required by medical staff to prepare each new patient to start the medical treatment (row 25). In addition, the amount of preparation time for the current week required by medical staff to prepare each new patient to start the medical treatment can further be broken down by amount of preparation time required by doctor (e.g., allergist), nurse practitioner/physician's assistant, and registered nurse/ medical assistant as shown in rows 33, 36, and 39 of FIG.

5B based on the estimated input received by the system for each one of the medical staff. Essentially, instead of using the total hours, the individual specialty hours can be multiplied by the number of new patients starting medical treatment for a given week.

In some embodiments, the system can also calculate the amount of time required by the medical staff to administer an initial dose of medical treatment to patients each week utilizing three separate received inputs: (1) the estimated amount of time required by medical staff to administer an initial dose of medical treatment to a patient; (2) the percentage of patients that are monitored by a group; and (3) the number of new patients starting medical treatment. The system can first determine if any of the patients are monitored as a group, if so, the percentage of patients being monitored together can be treated as one patient and the other patients treated separately. Accordingly, the system can then multiply the number of different patients (grouped together patients are treated as one) by the received estimated amount of time required by medical staff to administer an initial dose of medical treatment to a patient to calculate the amount of initial dose time per week required by medical staff. In addition, the amount of time required by the medical staff to administer an initial dose of medical treatment to patients each week can further be broken down by amount of time required by doctor (e.g., allergist), nurse practitioner/physician's assistant, and registered nurse/medical assistant. Essentially, instead of using the total hours, the individual specialty hours can be multiplied by the number of new patients starting medical treatment for a given week.

The following provides an example of the calculation for the amount of initial dose time (per week) required by medical staff to administer initial doses of medical treatment for the patients. After the system receives the various inputs shown in FIG. 2, the weekly initial dose hours (row 13) shown in FIG. 5A can be multiplied by the number of new patients anticipated in the next week (row 10) to calculate the amount of initial dose time for the current week required by medical staff to administer initial doses of medical treatment to the patients (row 26). If three patients are receiving an initial dose in a given week, but two of the patients will be seen/monitored as a group, then the system can treat this as if only two patients (technically 1.5 patients) are receiving the initial dose in the given week. In addition, the amount of time required by the medical staff to administer an initial dose of medical treatment to patients each week can further be broken down by amount of initial dose time required by doctor (e.g., allergist), nurse practitioner/physician's assistant, and registered nurse/medical assistant as shown in rows 31, 34, and 37 of FIG. 5B based on the estimated input received by the system for each one of the medical staff.

In some embodiments, the system can also calculate the amount of time required by the medical staff to administer subsequent dose escalation of medical treatment to patients each week by three separate received inputs: (1) the estimated amount of time required by medical staff to administer subsequent dose escalation of medical treatment per patient per visit; (2) the percentage of patients that are monitored by a group; and (3) the number of patients currently on dose escalation. The system can first determine if any of the patients are monitored as a group, if so, the percentage of patients being monitored together can be treated as one patient and the other patients treated separately. Accordingly, the system can then multiply the number of different patients that are currently on dose escalation (grouped together patients are treated as one) by the received estimated amount of time required by medical staff to administer subsequent dose escalation of medical treatment per patient per visit to calculate the amount of time required by medical staff to administer dose escalation each week. In addition, the amount of time required by the medical staff to administer subsequent dose escalation of medical treatment to patients each week can further be broken down by amount of time required by doctor (e.g., allergist), nurse practitioner/physician's assistant, and registered nurse/medical assistant. Essentially, instead of using the total hours, the individual specialty hours can be multiplied by the number of patients currently on dose escalation for a given week.

The following provides an example of the calculation for the amount of subsequent dose escalation time (per week) required by medical staff to administer subsequent dose escalation of medical treatment to patients. After the system receives the various inputs shown in FIG. 2, the weekly subsequent dose escalation hours (row 14) shown in FIG. 5A can be multiplied by the total patients treated (row 23) to calculate the amount of subsequent dose escalation time for the current week required by medical staff to administer subsequent doses of medical treatment to the patients (row 27). If three patients are receiving subsequent dose escalation in a given week, but two of the patients will be seen/monitored as a group, then the system will treat this as if only two patients (technically 1.5 patients) are receiving subsequent dose escalation in the given week. In addition, the amount of time required by the medical staff to administer subsequent dose escalation of medical treatment to patients each week can further be broken down by amount of subsequent dose time required by doctor (e.g., allergist), nurse practitioner/physician's assistant, and registered nurse/medical assistant as shown in rows 32, 35, and 38 of FIG. 5B based on the estimated input received by the system for each one of the medical staff.

In some embodiments, the system can calculate the time per predetermined time period (e.g., a week) required by medical staff to administer treatment to a single patient taking into account the number of visits to complete the medical treatment and the time between visits. For example, the total visit time for a patient at a treatment location for the first week can be about 7 hours which includes 5 hours of administering an initial dose of medical treatment on the first day and 2 hours of subsequent dose escalation on the second day. On the third week, the patient can return for another subsequent dose escalation visit which can take two hours. In this example, with 12 visits required for a patient to complete medical treatment and 14 days between visits, it can take a total of 22 weeks ((12−1)*14/7=22) (or 23 if a visit for maintenance is required) to complete treatment. If more days are required in between visits, the system can account for that by rounding the days to the next week. For example, if 16 days are required between visits with 12 visits total, the total weeks to complete would be 16*(12−1)/7=25.1 weeks, which can round up to 26 weeks. The system can also account for the attrition curve on an individual patient basis. Thus, if it's assumed that 80% of the patients will be left at the end of the up-dosing regimen (i.e., 80% of hours), and there is 1 patient and the dose escalation (DE) is 2, at the end of treatment only 1.6 hours would be required.

In some embodiments, the system can then calculate the time (e.g., hours per week) of active patient treatment (i.e., initial dose and subsequent dose escalation) as well as the time (e.g., hours per week) of active patient treatment and patient preparation. The total time for active patient treatment can be calculated by the summation of the amount of initial dose administration time required by medical staff and the amount of time required by medical staff to administer dose escalation. The total time for active patient treatment and patient preparation can be calculated by the summation of the amount of initial dose administration time required by medical staff, the amount of time required by medical staff to administer subsequent dose escalation each week, and the amount of preparation time per week required by medical staff to prepare each new patient to start the medical treatment. The calculations in this paragraph can further be broken down by amount of time required by doctor (e.g., allergist), nurse practitioner/physician's assistant, and registered nurse/medical assistant instead of total for medical staff.

In some embodiments, the system can sum the amount of time per week required by the medical staff to prepare patients to start the medical treatment, the amount of time per week required by medical staff to administer an initial dose of medical treatment to patients, and the amount of time per week required by medical staff to administer subsequent dose escalation of the medical treatment to the patients in order to calculate the total time per week required for medical staff to administer medical treatment to the patients. This is shown in row 29 of FIG. 5B.

At block 122, in some embodiments, the system may receive the number of areas at a treatment location dedicated to the medical treatment as well as the amount of available treatment time per area per the predetermined time period. The area dedicated to the medical treatment can be any area in a treatment location that is dedicated to treating patients with the specific medical treatment (e.g., an examination room). Such areas are often necessary as the medical staff may need to administer the medical treatment and monitor the patients in an area without risking exposure of the patients to other factors. In some embodiments, the system can receive the number of areas dedicated to OIT. As discussed above, these areas can be examination rooms dedicated to administering the medical treatment to patients. For example, FIGS. 2 and 8F provide an example of an input for the number of exam rooms that are dedicated to a peanut allergy medical treatment such as Palforzia.

In some embodiments, the number of areas dedicated to the medical treatment can also include the amount of time available per area dedicated to the medical treatment per predetermined time period at a given treatment location. In some embodiments, the amount of time available per area dedicated to the medical treatment per week at a given treatment location is an estimate. As shown in FIG. 2, the total estimated hours available per area dedicated to the medical treatment can be input into the user interface.

At block 124, the system can then determine the available treatment time for all areas at the treatment location dedicated to the medical treatment over the selected time period. For example, the system can multiply the number of areas at the treatment location dedicated to the medical treatment with the amount of available treatment time per area to determine the available treatment time for all areas at the treatment location dedicated to the medical treatment over the selected time period. In some embodiments, the available treatment time for all areas at the treatment location dedicated to the medical treatment can be the same over all time periods.

At block 126, the system, in some embodiments, can determine when the time required by medical staff to administer medical treatment to the patients exceeds the available treatment time for all areas at the treatment location dedicated to the medical treatment over the selected period of time. In some embodiments, the time required by medical staff to administer medical treatment to patients can just be the active patient treatment (i.e., time required by medical staff to administer initial dose to patients and time required by medical staff to administer subsequent dose escalation to patients). In some embodiments, the system can determine when the time required by medical staff to administer active patient treatment exceeds the available treatment time for all areas at the treatment location.

Figure 6A:
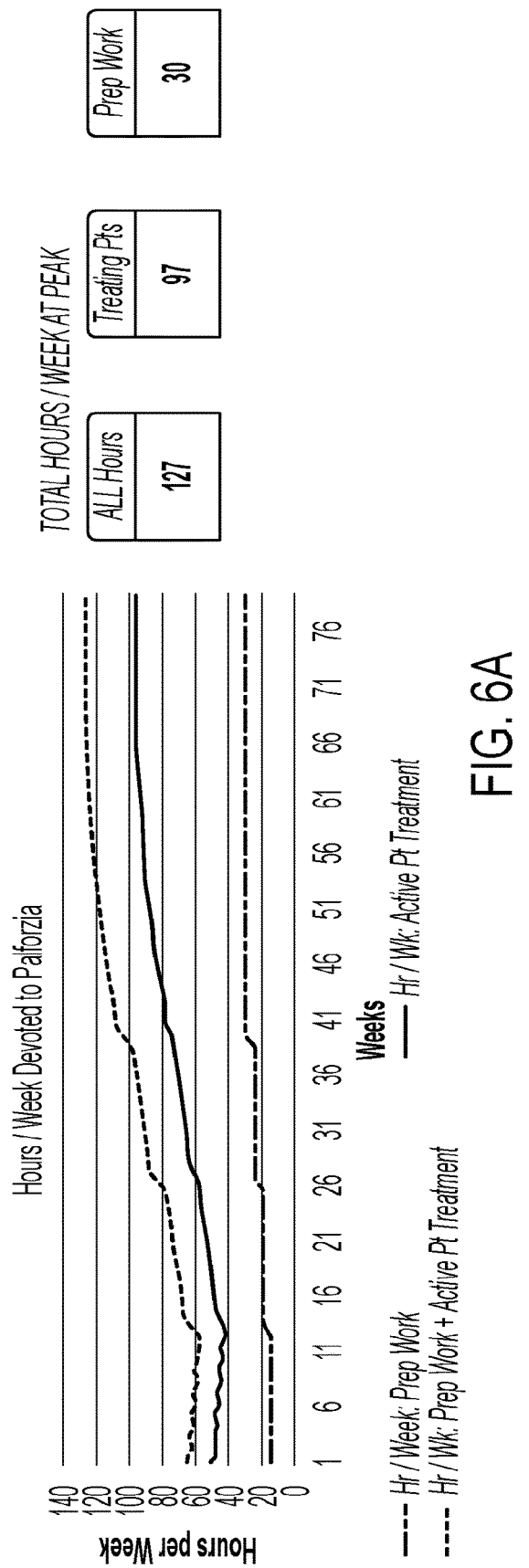
FIG. 6A depicts a first exemplary graphical indication of the medical staffing system, in accordance with some embodiments.
Figure 6B:
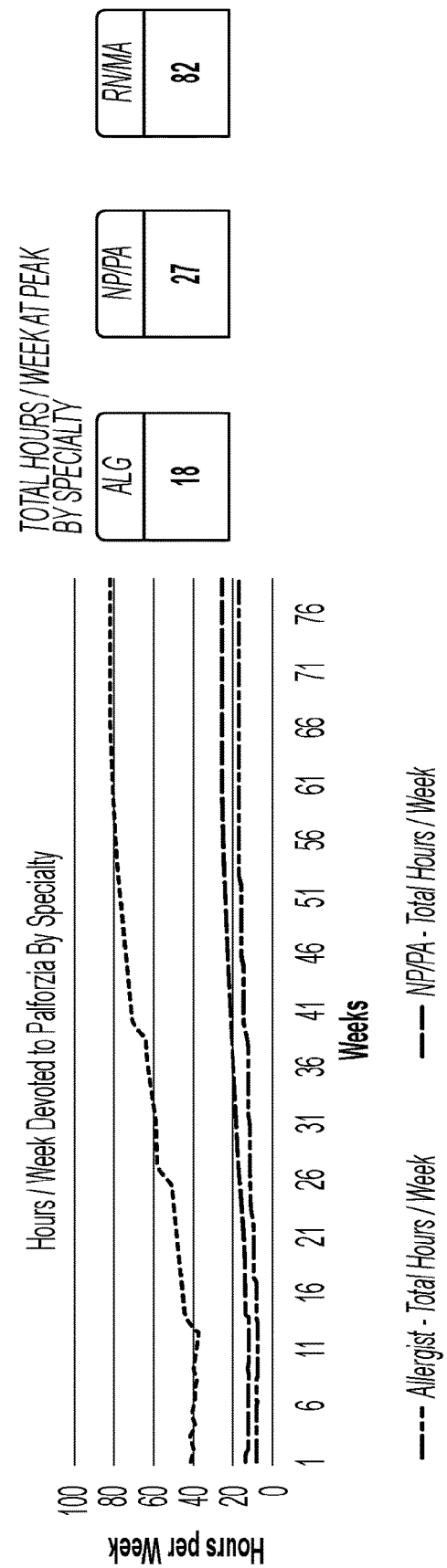
FIG. 6B depicts a second exemplary graphical indication of the medical staffing system, in accordance with some embodiments.
Figure 9A:
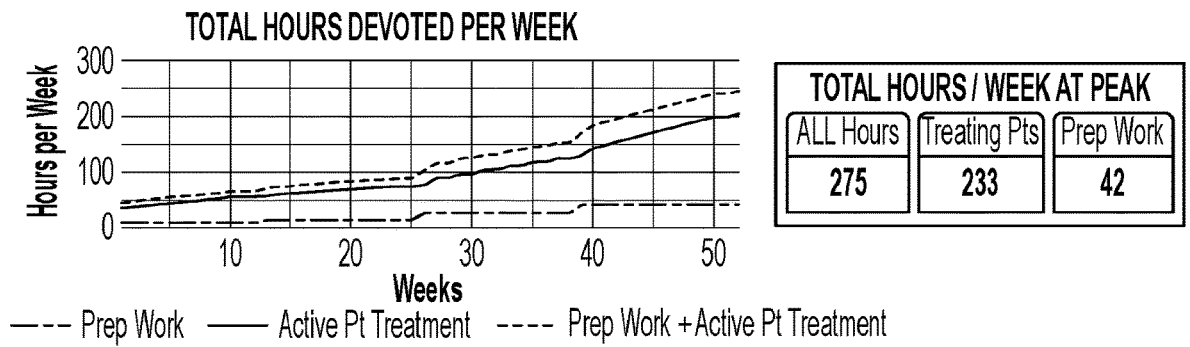
FIG. 9A depicts a fifth exemplary graphical indication of the medical staffing system, in accordance with some embodiments.
Figure 9B:
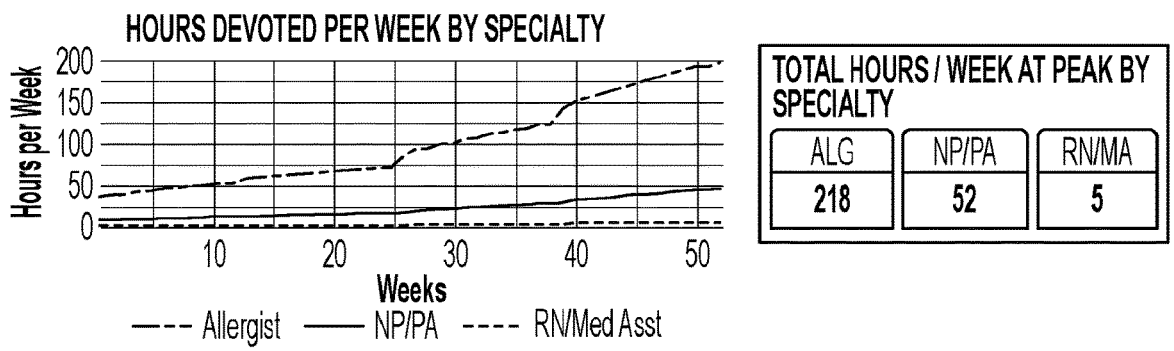
FIG. 9B depicts a sixth exemplary graphical indication of the medical staffing system, in accordance with some embodiments.

At block 128, the system, in some embodiments, can display a graphical indication of the time required by medical staff to administer medical treatment to the patients at the treatment location over the selected time period. In some embodiments, the graphical indication can be a graph of medical staff required time per predetermined time period vs. the selected time period. An example of a graphical indication of the time required by medical staff to administer medical treatment (e.g., Palforzia) to the patients at the treatment location over the selected time period is shown in FIGS. 6A and 9A. The display can further be broken down by specialty (i.e., doctor/allergist, RN/Med Assistant, and NP/PA). FIGS. 6B and 9B illustrate example of a graphical indication of the time required by medical staff specialty to administer medical treatment (e.g., Palforzia) to the patients at the treatment location over the selected time period. These Figures can provide a medical staff with the amount of hours they need to have someone staffed in order to handle the amount of patients undergoing medical treatment for a given treatment location. FIGS. 6A-6B and 9A-9B also show the hours per week required for preparation work for new patients as well as active patient treatment (i.e., initial dose administering and subsequent dose escalation) and total hours.

In some embodiments, the system can also notify the medical staff of the time required by medical staff to administer medical treatment to the patients at the treatment location over the selected time period. For example, the staffing system can include contact information for the medical staff at a treatment location and can notify those members of the medical staff when they are required to be at the treatment location in order to meet the time requirements to administer medical treatment to the patients at the treatment location over the selected time period. In some embodiments, the staffing system can create a work schedule for the medical staff at a treatment location to meet the time requirements to administer medical treatment to the patients at the treatment location over the selected time period.

In some embodiments, the system can display the total hours per week administering medical treatment to patients by the medical staff as well as by individual specialties of the medical staff at peak. The system can determine the peak by finding the highest point (most hours per week) along the preparation work curve. The week where the highest point along the preparation work curve can be used to find the peak week for the total hours curve, the treating active patients curve, as well as the individual specialty hour per week curves. In some embodiments, the "peak" can be calculated only within the 52-week timeframe.

At block 130, the system, in some embodiments, can display a graphical indication of the available treatment time for all areas at the treatment location dedicated to the medical treatment over the selected time period. An example of a graphical indication of the available treatment time for all areas at the treatment location dedicated to the medical treatment over the selected time period is shown in FIGS. 6C and 9C.

At block 132, the system, in some embodiments, can display a graphical indication that the time required by medical staff to administer medical treatment to the patients exceeds the available treatment time for all areas at the treatment location dedicated to the medical treatment over the selected period of time. In some embodiments, the graphical indication can provide a warning to users of the system that they will not have enough dedicated areas to medical treatment during a certain time period to handle all the patients at the given treatment location as shown in FIGS. 6C and 9C. As such, the system can inform users when there will not be enough areas dedicated to the medical treatment to accommodate the active patient treatment (i.e., initial dose administration and dose escalation). Thus, the medical staff or treatment location can take action to prevent this issue from occurring by either dedicating more areas for the medical treatment and/or taking on less patients.

Figure 6C:
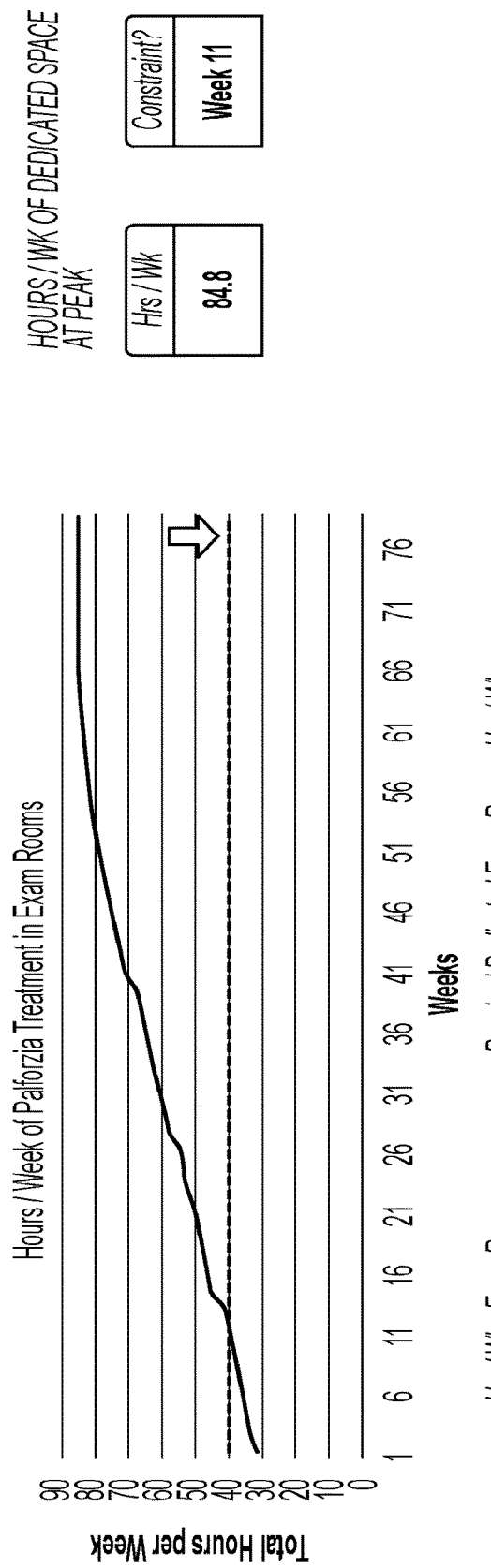
FIG. 6C depicts a third exemplary graphical indication of the medical staffing system, in accordance with some embodiments.
Figure 6D:
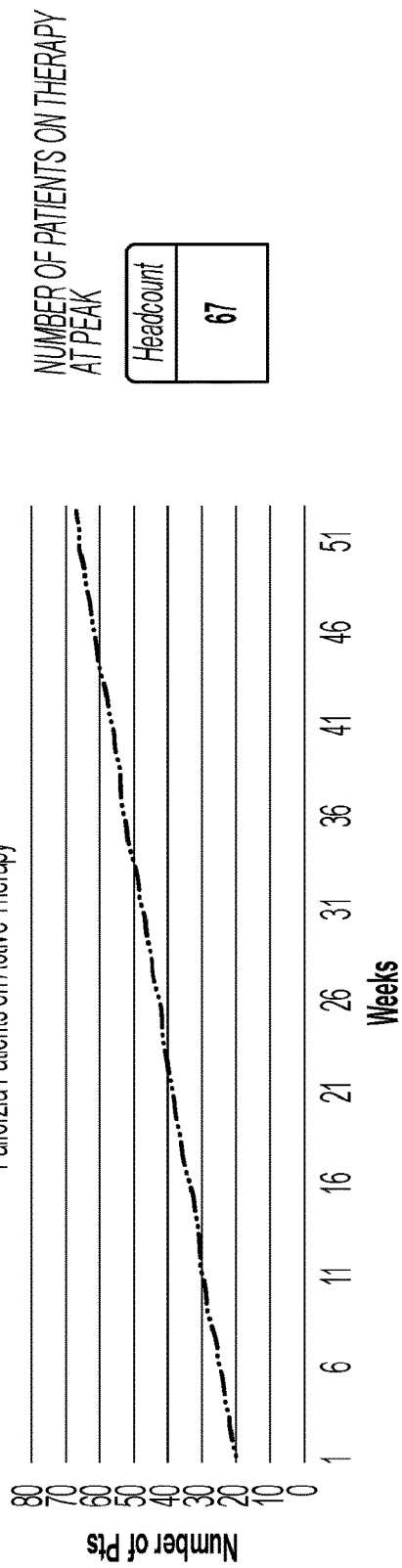
FIG. 6D depicts a fourth exemplary graphical indication of the medical staffing system, in accordance with some embodiment.
Figure 9C:
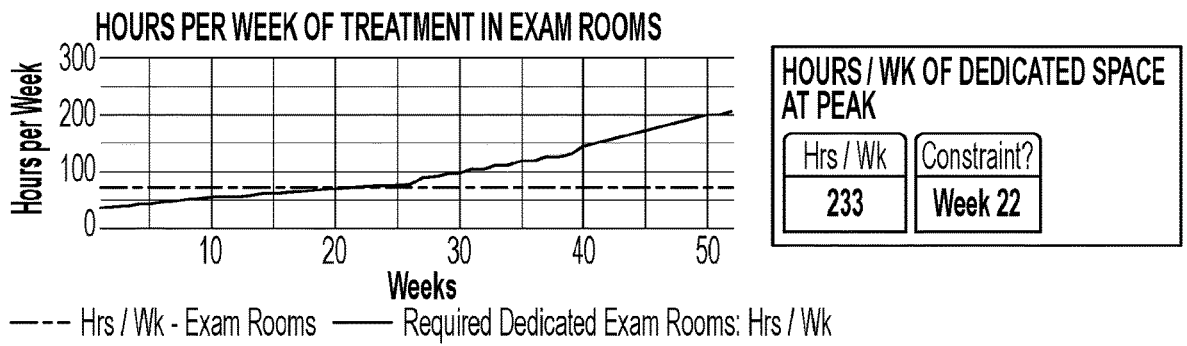
FIG. 9C depicts a seventh exemplary graphical indication of the medical staffing system, in accordance with some embodiments.
Figure 9D:
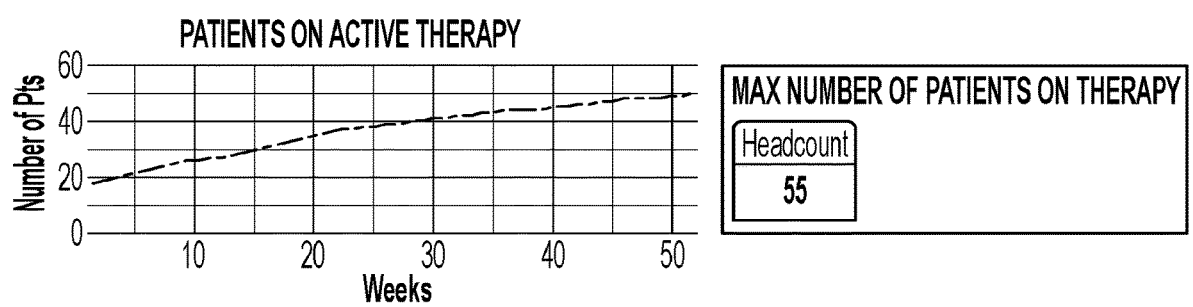
FIG. 9D depicts an eighth exemplary graphical indication of the medical staffing system, in accordance with some embodiment.

In some embodiments, the system can calculate when (i.e., what week) the time required by medical staff to administer medical treatment to the patients exceeds the available treatment time for all areas at the treatment location dedicated to the medical treatment by determining when the curve for time required by medical staff to administer medical treatment to the patients at the treatment location intersects the curve for available treatment time for all areas at the treatment location shown in FIGS. 6C and 9C. At block 134, in some embodiments, the system can display a graphical indication of the number of patients undergoing medical treatment at the treatment location over the selected time period as shown in FIGS. 6D and 9D. In some embodiments, the system can display a graphical indication of the number of patients undergoing medical treatment at steady state as explained above.

Example

Figure 10:
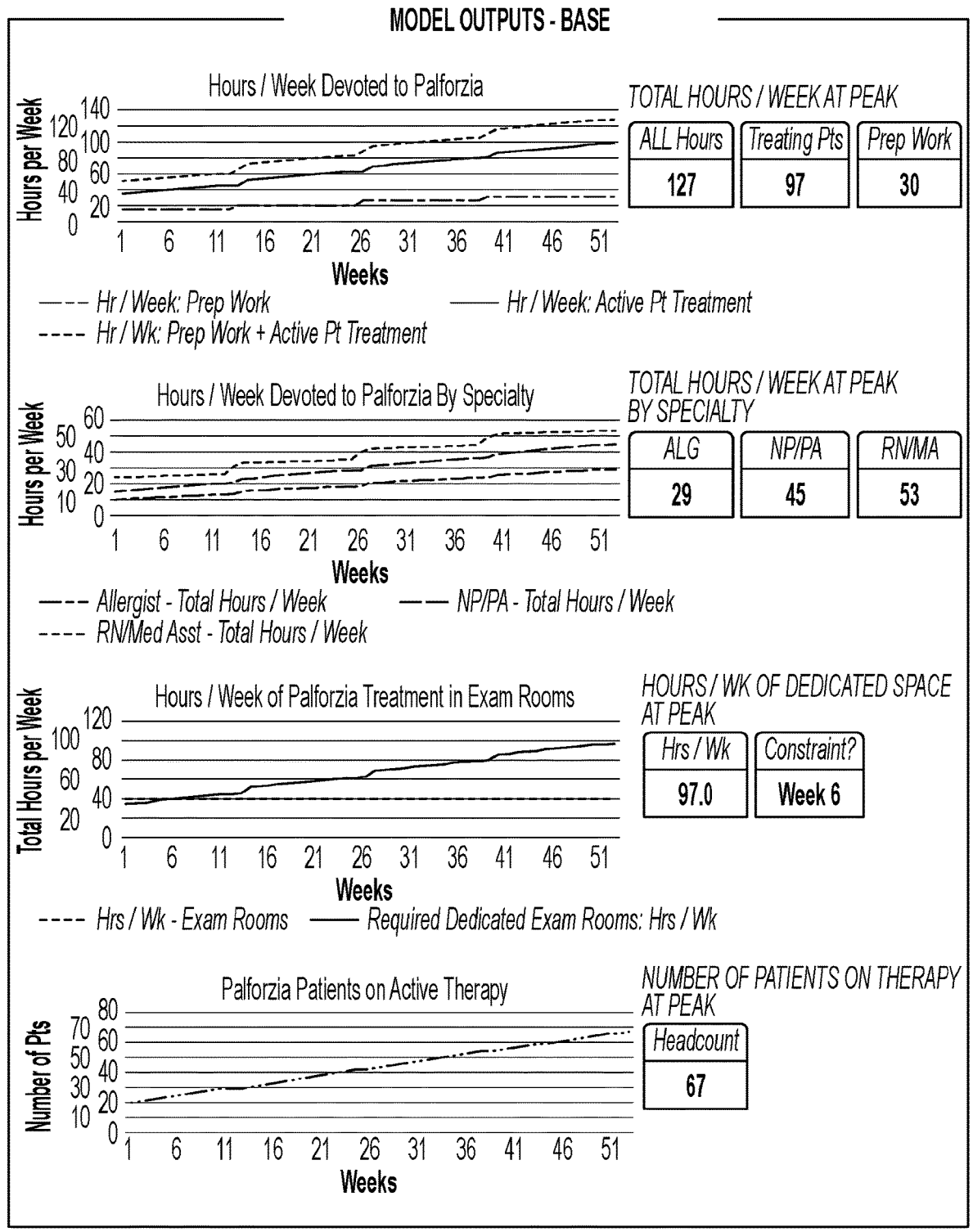
FIG. 10 depicts exemplary graphical indications of the medical staffing system of the Example described herein.

The following is a walk-through example of a peak week determination/calculation described herein. The following example took into account the various inputs shown in FIG. 2 and calculates the various outputs at subsequent weeks. With those inputs, the outputs are shown in FIG. 10.

First, the time required by medical staff to administer medical treatment (e.g., Palforzia) to the patients at the treatment location at peak week (i.e., week 78) can be calculated. The medical staffing system can look back 2 quarters, so the peak week (in the Example) can be the last calendar week 78 (26 weeks of previous quarter+52 weeks of current year). This calculation can be shown in FIG. 11. Specifically, row 29 shows 127 hours at peak which is the sum of "Hr/Week: Prep Work" (row 25, 30 hours) and "Hr/Wk: Active Pt Treatment" (row 28, 97 hours). The "Hr/Wk: Active Pt Treatment" is the sum of "Total IDE per week (Supervised Hours)" (30 hours) and "Total DE per week (Supervised Hours)" (67 hours). The "Total IDE per week" can be calculated because there are 6 new patients per week in Q4 that each require 5 hours of initial dose escalation (i.e., 6*5=30 hours). The "Total DE per week" can be calculated by looking to see if any patients are first monitored as a group, then multiply by the DE hour required by the number of groups. In this example, 0% of the patients are monitored as a group, so in this week there are 67 patients in total (row 23) times 1 hour DE per patient equals 67 total hours.

Second, the time required by medical staff specialty (i.e., doctor/allergist, RN/Med Assistant, and NP/PA) registered nurse to administer medical treatment (e.g., Palforzia) to the patients at the treatment location at peak week can be calculated. This calculation is shown in FIG. 12. Specifically, row 40 shows the total hours for the allergist/doctor which is the sum of the IDE hours/week, DE hours/week, and Prep hours/week for the allergist/doctor (rows 31-33). The IDE hours/week for the allergist (row 31) can be calculated by the total IDE per week (30 hours in week 78) times the percentage of hours of IDE worked on by the allergist/doctor (1.25 ALG hours/5 total hours=25%) which equals 7.5 hours of IDE hours done by the allergist/doctor. The DE hours/week for the allergist/doctor (row 32) can be calculated by multiplying the total DE hours per week (67 hours in week 78) times the percentage of hours of DE worked on by the allergist/doctor (0.3 ALG hours/1 total hours=30%) which equals 20.1 hours of DE done by the allergist/doctor. Lastly, the Prep hours/week for the allergist/doctor (row 33) can be calculated by multiplying the total prep hours per week (30 hours in week 78) times the percentage of hours of DE worked on by the allergist/doctor (0.25 ALG hours/5 total hours=5%) which equals 1.5 hours of Prep work done by the allergist/doctor. The same calculations can be done for the NP/PA hours and the RN/MA hours.

Third, the available treatment time for all areas at the treatment location dedicated to the medical treatment at peak week can be calculated. This calculation is shown in FIG. 13. This can be calculated by measuring the "Required Dedicated Exam Rooms: Hrs/wk" as shown in cell CA7 in FIG. 13. The hours/week needed in the exam rooms is the same calculation as the Hr/Wk: Active Pt Treatment shown in row 28, as explained above. However, there is a constraint that looks at the week at which the available exam room hours each week is exceeded by the number of patient hours needed such that the practice manager or whoever is in charge of the treatment location can plan accordingly if the capacity cannot meet the demand. For example, the staffing system can look up a flag such as that shown in row 8 and evaluation the following scenarios: (1) If the capacity is already being exceeded in the prior quarters, the cell can display "Week 1" as a warning; (2) If the capacity is not exceeded throughout the planning horizon, the cell can display "No"; and (3) If the capacity is exceeded in the current planning horizon, it can display the week when the capacity is exceeded (In this example, in week 6, since the IDE+DE hours are exceeding the total capacity of 40 hours, the cell displays the message, "Week 6").

Lastly, the number of patients undergoing medical treatment at the treatment location at peak week can be calculated. This calculation is shown in FIG. 14. This can be calculated by summing up the number of patients starting in week 78 (i.e., peak week) and counting backwards every two weeks the past patients who are still in the updosing stage. This takes into account that (according to the input) 6 patients start arriving in Q4, but in Q3, there are 5 patients assumed each week. So the staffing system can sum up diagonally, starting from week 78 and counting backwards: 6 patients in week 78, 6 patients from week 76, 6 from week 74 . . . 6 from week 66, 5 from week 64 . . . 5 from week 56, which is the last patients still on updosing. Summing them will give you 67 patients in total.

Figure 7:
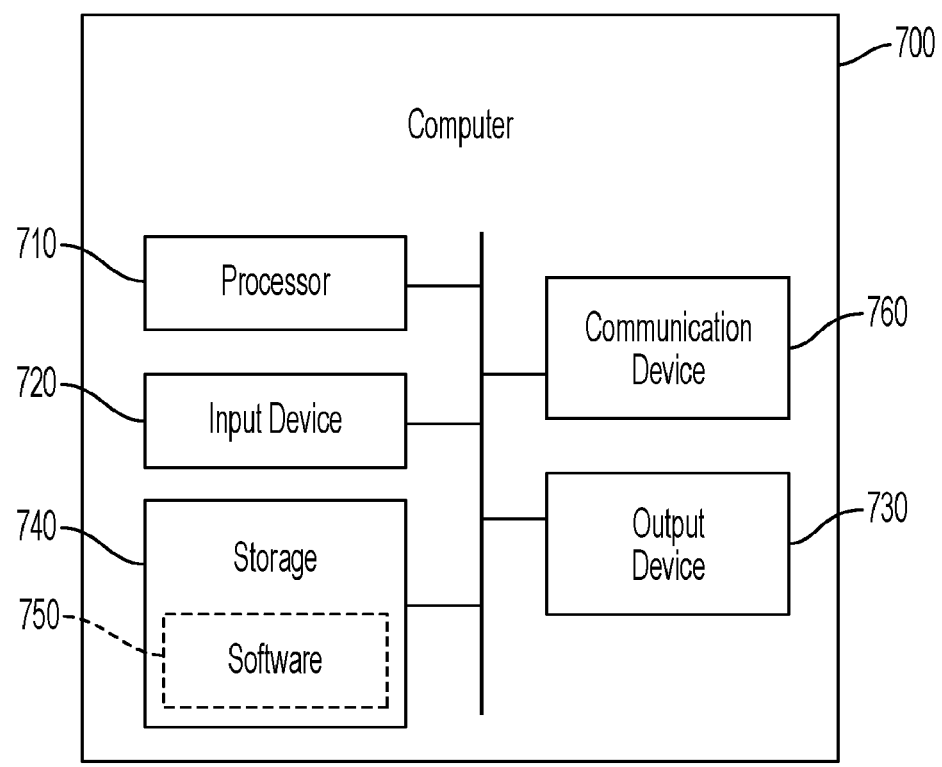
FIG. 7 depicts a computer, in accordance with some embodiments.

FIG. 7 illustrates a computer, in accordance with some embodiments. Computer 700 can be a component of a system for determining medical staffing requirements for administering medical treatment. In some embodiments, computer 700 may be configured to execute a method for determining medical staffing requirements for administering medical treatment, such as all or part of method 100 described above with respect to FIGS. 1A-1B.

Computer 700 can be a host computer connected to a network. Computer 700 can be a client computer or a server. As shown in FIG. 7, computer 700 can be any suitable type of microprocessor-based device, such as a personal computer; workstation; server; or handheld computing device, such as a phone or tablet. The computer can include, for example, one or more of processor 710, input device 720, output device 730, storage 740, and communication device 760.

Input device 720 can be any suitable device that provides input, such as a touch screen or monitor, keyboard, mouse, or voice-recognition device. Output device 730 can be any suitable device that provides output, such as a touch screen, monitor, printer, disk drive, or speaker. In some embodiments, the output can be a document such as a Microsoft Word or pdf document.

Storage 740 can be any suitable device that provides storage, such as an electrical, magnetic, or optical memory, including a RAM, cache, hard drive, CD-ROM drive, tape drive, or removable storage disk. Communication device 760 can include any suitable device capable of transmitting and receiving signals over a network, such as a network interface chip or card. The components of the computer can be connected in any suitable manner, such as via a physical bus or wirelessly. Storage 740 can be a non-transitory computer-readable storage medium comprising one or more programs, which, when executed by one or more processors, such as processor 710, cause the one or more processors to execute methods described herein, such as all or part of method 100 described above with respect to FIGS. 1A-1B.

Software 750, which can be stored in storage 740 and executed by processor 710, can include, for example, the programming that embodies the functionality of the present disclosure (e.g., as embodied in the systems, computers, servers, and/or devices as described above). In some embodiments, software 750 can be implemented and executed on a combination of servers such as application servers and database servers.

Software 750 can also be stored and/or transported within any computer-readable storage medium for use by or in connection with an instruction execution system, apparatus, or device, such as those described above, that can fetch and execute instructions associated with the software from the instruction execution system, apparatus, or device. In the context of this disclosure, a computer-readable storage medium can be any medium, such as storage 740, that can contain or store programming for use by or in connection with an instruction execution system, apparatus, or device.

Software 750 can also be propagated within any transport medium for use by or in connection with an instruction execution system, apparatus, or device, such as those described above, that can fetch and execute instructions associated with the software from the instruction execution system, apparatus, or device. In the context of this disclosure, a transport medium can be any medium that can communicate, propagate, or transport programming for use by or in connection with an instruction execution system, apparatus, or device. The transport-readable medium can include, but is not limited to, an electronic, magnetic, optical, electromagnetic, or infrared wired or wireless propagation medium.

Computer 700 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computer 700 can implement any operating system suitable for operating on the network. Software 750 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A method for determining medical staffing requirements for administering an oral immunotherapy (OIT) for peanut allergy to patients at a treatment location, wherein the OIT for peanut allergy comprises an up-dosing protocol and one or more maintenance doses, the method comprising:
   1) Receiving:
      i) a number of patients starting the OIT per a selected time period at a treatment location;
      ii) a number of visits to the treatment location to complete the up-dosing protocol and/or the one or more maintenance doses;
      iii) an amount of time between visits to the treatment location to complete the up-dosing protocol and/or the one or more maintenance doses;
      iv) a number of rooms or areas available at the treatment location designated for the OIT for peanut allergy; and
      v) a number of medical staff present at the treatment location;
   2) Determining:
      i) an estimated amount of time required by the number of medical staff to administer the up-dosing protocol and/or the one or more maintenance doses, comprising:
         a first estimated amount of time to administer an initial dose escalation (IDE) of the up-dosing protocol for each new patient and which of these patients can be monitored as a group;
         a second estimated amount of time to administer each subsequent dose of a dose escalation of the up-dosing protocol and which of these patients can be monitored as a group;
      ii) an available treatment time for the number of rooms or areas over the selected time period;

iii) a number of visits to the treatment location required for each patient to complete the up-dosing protocol and/or one or more maintenance doses;

iv) an amount of time between visits to the treatment location for each patient after the current administration by the medical staff;

v) an amount of time to administer a subsequent dose for each patient;

vi) a percentage of patients who completed the up-dosing protocol and/or one or more maintenance doses;

vii) when the time required by the number of medical staff to administer the up-dosing protocol and/or the one or more maintenance doses to the patients exceeds the available treatment time for all rooms or areas at the treatment location designated for the OIT for peanut allergy over the selected period of time; and vii when steady state occurs, wherein steady state is when a rate of new patients equals a rate of patients completing the OIT; and 3) displaying, using a graphical indication,
i) the estimated amount of time for the number of medical staff to administer the up-dosing protocol and/or the one or more maintenance doses to each patient and the room or area at the treatment location for administration over the selected time period;

ii) the available treatment time for each room or area dedicated to the OIT over the selected time period;

iii) the number of visits to the treatment location required for each patient to complete the up-dosing protocol and/or one or more maintenance doses after the current administration;

iv) the amount of time to administer the subsequent dose for each patient;

v) the amount of time between visits to the treatment location for each patient after the current administration by the medical staff;

vi) the number of patients undergoing the OIT at the treatment location over the selected time period;

vii) the percentage of patients who completed the up-dosing protocol and/or one or more maintenance doses after the administration;

viii) that the time required by the number of medical staff to administer the up-dosing protocol and/or the one or more maintenance doses to the patients exceeds the available treatment time for all rooms or areas at the treatment location designated for the OIT for peanut allergy over the selected period of time; and vix) if steady state occurs and the number of patients undergoing OIT at steady state.

2. The method of claim 1, further comprising:
receiving the number of rooms or areas at the treatment location dedicated to the OIT and an amount of available treatment time per room or area per the selected time period;
determining available treatment time for all rooms or areas at the treatment location dedicated to the OIT over the selected time period; and
displaying, using a graphical indication, an available treatment time for all rooms or areas at the treatment location dedicated to the OIT over the selected time period.

3. The method of claim 1, wherein displaying, using the graphical indication, the number of patients undergoing the OIT for peanut allergy at the treatment location over the selected time period comprises displaying a number of patients undergoing the up-dosing protocol and/or one or more maintenance doses.

4. The method of claim 1, further comprising receiving the estimated percentage of patients who complete the up-dosing protocol and/or one or more maintenance doses, wherein determining the number of patients undergoing the up-dosing protocol and/or one or more maintenance doses at the treatment location over the selected time period is further based on the estimated percentage of patients who complete the up-dosing protocol and/or one or more maintenance doses.

5. The method of claim 1, wherein determining the estimated amount of time required by the number of medical staff to administer the up-dosing protocol and/or the one or more maintenance doses comprises determining, per patient per visit to the treatment location, an estimated amount of time required by the number of medical staff to prepare a patient to start the up-dosing protocol and/or one or more maintenance doses.

6. The method of claim 5, further comprising determining an estimated percentage of patients being monitored as a group.

7. The method of claim 1, further comprising notifying the number of medical staff of the time required to administer the up-dosing protocol and/or the one or more maintenance doses to the patients at the treatment location over the selected time period.

8. The method of claim 1, wherein the number of medical staff comprises at least one of a doctor, a nurse practitioner or physician's assistant, or a registered nurse or medical assistant.

9. A system for determining medical staffing requirements for administering an oral immunotherapy (OIT) for peanut allergy to patients at a treatment location, wherein the OIT for peanut allergy comprises an up-dosing protocol and one or more maintenance doses, the system comprising:
a computer-readable storage medium, one or more processors, and one or more output devices, wherein the system is configured to store, using the computer-readable storage medium, instructions, which when executed by the one or more processors:
1) Receive:
i) a number of patients starting the OIT per a selected time period at a treatment location;
ii) a number of visits to the treatment location to complete the up-dosing protocol and/or the one or more maintenance doses;
iii) an amount of time between visits to the treatment location to complete the up-dosing protocol and/or the one or more maintenance doses;
iv) a number of rooms or areas available at the treatment location designated for the OIT for peanut allergy; and
v) a number of medical staff present at the treatment location;
2) Determine:
i) an estimated amount of time required by the number of medical staff to administer the up-dosing protocol and/or the one or more maintenance doses, comprising:
a first estimated amount of time to administer an initial dose escalation (IDE) of the up-dosing protocol for each new patient and which of these patients can be monitored as a group;
a second estimated amount of time to administer each subsequent dose of a dose escalation of the up-dosing protocol and which of these patients can be monitored as a group;
ii) an available treatment time for the number of rooms or areas over the selected time period;
iii) a number of visits to the treatment location required for each patient to complete the up-dosing protocol and/or one or more maintenance doses;
iv) an amount of time between visits to the treatment location for each patient after the current administration by the medical staff;
v) an amount of time to administer a subsequent dose for each patient;
vi) a percentage of patients who completed the up-dosing protocol and/or one or more maintenance doses;
vii) when the time required by the number of medical staff to administer the up-dosing protocol and/or the one or more maintenance doses to the patients exceeds the available treatment time for all rooms or areas at the treatment location designated for the OIT for peanut allergy over the selected period of time; and
viii) when steady state occurs, wherein steady state is when a rate of new patients equals a rate of patients completing the OIT; and
3) display, using a graphical indication, of
i) the estimated amount of time for each medical staff to administer the up-dosing protocol and/or the one or more maintenance doses to each patient and the room or area at the treatment location for administration over the selected time period;
ii) the available treatment time for each room or area dedicated to the OIT over the selected time period;
iii) the number of visits to the treatment location required for each patient to complete the up-dosing protocol and/or one or more maintenance doses after the current administration;
iv) the amount of time to administer the subsequent dose administration for each patient;
v) the amount of time between visits to the treatment location for each patient after the current administration by the medical staff;
vi) the number of patients undergoing the OIT at the treatment location over the selected time period;
vii) the percentage of patients who completed the up-dosing protocol and/or one or more maintenance doses after the administration
viii) that the time required by the number of medical staff to administer the up-dosing protocol and/or the one or more maintenance doses to the patients exceeds the available treatment time for all rooms or areas at the treatment location designated for the OIT for peanut allergy over the selected period of time; and
vix) if steady state occurs and the number of patients undergoing OIT at steady state.

10. A non-transitory computer-readable storage medium storing one or more programs, the one or more programs comprising instructions for determining medical staffing requirements for administering an oral immunotherapy (OIT) for peanut allergy to patients at a treatment location, wherein the OIT for peanut allergy comprises an up-dosing protocol and one or more maintenance doses, which when executed by an electronic device, cause the device to:
1) Receive:
i) a number of patients starting OIT per a selected time period at a treatment location;
ii) a number of visits to the treatment location to complete the up-dosing protocol and/or the one or more maintenance doses;
iii) an amount of time between visits to the treatment location to complete the up-dosing protocol and/or the one or more maintenance doses;
iv) a number of rooms or areas available at the treatment location designated for the OIT for peanut allergy; and
v) a number of medical staff present at the treatment location;
2) Determine:
i) an estimated amount of time required by the number of medical staff to administer the up-dosing protocol and/or the one or more maintenance doses, comprising:
a first estimated amount of time to administer an initial dose escalation (IDE) of the up-dosing protocol for each new patient and which of these patients can be monitored as a group;
a second estimated amount of time to administer each subsequent dose of a dose escalation of the up-dosing protocol and which of these patients can be monitored as a group;
ii) an available treatment time for the number of rooms or areas over the selected time period;
iii) a number of visits to the treatment location required for each patient to complete the up-dosing protocol and/or one or more maintenance doses;
iv) an amount of time between visits to the treatment location for each patient after the current administration by the medical staff;
v) an amount of time to administer a subsequent dose for each patient;
vi) a percentage of patients who completed the up-dosing protocol and/or one or more maintenance doses;
vii) when the time required by the number of medical staff to administer the up-dosing protocol and/or the one or more maintenance doses to the patients exceeds the available treatment time for all rooms or areas at the treatment location designated for the OIT for peanut allergy over the selected period of time; and
viii) when steady state occurs, wherein steady state is when a rate of new patients equals a rate of patients completing the OIT; and
3) display, using a graphical indication,
i) the estimated amount of time for each medical staff to administer the up-dosing protocol and/or the one or more maintenance doses to each patient and the room or area at the treatment location for administration over the selected time period;
ii) the available treatment time for each room or area dedicated to the OIT over the selected time period;
iii) the number of visits to the treatment location required for each patient to complete the up-dosing protocol and/or one or more maintenance doses after the current administration;
iv) the amount of time to administer the subsequent dose for each patient;
v) the amount of time between visits to the treatment location for each patient after the current administration by the medical staff;
vi) the number of patients undergoing the OIT at the treatment location over the selected time period;

vii) the percentage of patients who completed the up-dosing protocol and/or one or more maintenance doses after the administration
viii) that the time required by the number of medical staff to administer the up-dosing protocol and/or the one or more maintenance doses to the patients exceeds the available treatment time for all rooms or areas at the treatment location designated for the OIT for peanut allergy over the selected period of time; and
vix) if steady state occurs and the number of patients undergoing OIT at steady state.

* * * * *